United States Patent
June et al.

(10) Patent No.: US 9,161,971 B2
(45) Date of Patent: Oct. 20, 2015

(54) METHOD FOR TREATING CHRONIC LYMPHOCYTIC LEUKEMIA (CC)

(75) Inventors: Carl H. June, Merion Station, PA (US); Bruce Levine, Cherry Hill, NJ (US); Anne Chew, Cherry Hill, NJ (US); Stephen J. Schuster, Springfield, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 259 days.

(21) Appl. No.: 13/537,330

(22) Filed: Jun. 29, 2012

(65) Prior Publication Data
US 2012/0263693 A1     Oct. 18, 2012

Related U.S. Application Data

(62) Division of application No. 13/201,829, filed as application No. PCT/US2010/025239 on Feb. 24, 2010, now Pat. No. 8,415,150.

(60) Provisional application No. 61/155,026, filed on Feb. 24, 2009.

(51) Int. Cl.
*A61K 35/12* (2015.01)
*A61K 39/00* (2006.01)
*C12N 5/00* (2006.01)
*C12N 5/0783* (2010.01)

(52) U.S. Cl.
CPC .......... *A61K 39/0008* (2013.01); *C12N 5/0636* (2013.01); *A61K 2035/122* (2013.01); *A61K 2039/5158* (2013.01); *C12N 2501/51* (2013.01); *C12N 2501/515* (2013.01)

(58) Field of Classification Search
None
See application file for complete search history.

(56) References Cited

U.S. PATENT DOCUMENTS

| 7,402,431 | B2 | 7/2008 | Har-Noy | |
| 2003/0119185 | A1* | 6/2003 | Berenson et al. | 435/372 |
| 2003/0147869 | A1 | 8/2003 | Riley et al. | |
| 2003/0157514 | A1 | 8/2003 | Finger et al. | |
| 2003/0224520 | A1* | 12/2003 | June et al. | 435/455 |
| 2004/0005298 | A1* | 1/2004 | Bonyhadi et al. | 424/93.7 |
| 2004/0101519 | A1 | 5/2004 | June et al. | |
| 2004/0110290 | A1 | 6/2004 | June et al. | |
| 2006/0034810 | A1 | 2/2006 | Riley et al. | |
| 2008/0279861 | A1* | 11/2008 | Har-Noy | 424/154.1 |

FOREIGN PATENT DOCUMENTS

WO    WO 03/057171    7/2003

OTHER PUBLICATIONS

Foster et al. Best Practice & Res. Clin. Haematol. 21: 375-389, 2008.*
Porter et al. Blood. 2006; 107: 1325-1331.*
Liebowitz et al., Curr. Opin. Onc. 10:533-541, 1998.*
Bonyhadi et al., "In vitro engagement of CD3 and CD28 corrects T cell defects in chronic lymphocytic leukemia." 2005, J Immunol 174:2366-75.
Kalamasz et al., "Optimization of human T-cell expansion ex vivo using magnetic beads conjugated with anti-CD3 and Anti-CD28 antibodies." 2004, J Immunother 27:405-18.
Laport et al., "Adoptive transfer of costimulated T cells induces lymphocytosis in patients with relapsed/refractory non-Hodgkin lymphoma following CD34+-selected hematopoietic cell transplantation." 2003, Blood 102:2004-13.
Levine et al., "Effects of CD28 costimulation on long-term proliferation of CD4+ T cells in the absence of exogenous feeder cells." 1997, J. Immunol 159:5921-30.
Rapoport et al.., "Restoration of immunity in lymphopenic individuals with cancer by vaccination and adoptive T-cell transfer." 2005, Nat Med 11:1230-7.

* cited by examiner

*Primary Examiner* — Ilia Ouspenski

(74) *Attorney, Agent, or Firm* — Saul Ewing LLP; Kathryn Doyle; Kelly J. Morgan

(57) ABSTRACT

The present invention relates generally to the treatment of PML by infusion of activated and expanded autologous lymphocytes.

12 Claims, 7 Drawing Sheets

METHOD FOR TREATING CHRONIC LYMPHOCYTIC LEUKEMIA (CC)

CROSS-REFERENCE TO RELATED APPLICATION

The present application is a divisional of U.S. Patent Application No. 13/201,829, filed Oct. 26, 2011 which is a 35 U.S.C. §371 national phase application from, and claiming priority to, International Application No. PCT/US2010/025239, filed Feb. 24, 2010, which is entitled to priority under 35 U.S.C. §119(e) to U.S. Provisional Application No. 61/155,026, filed Feb. 24, 2009, all of which applications are hereby incorporated by reference herein in their entireties.

BACKGROUND OF THE INVENTION

Progressive multifocal leukoencephalopathy (PML), also known as progressive multifocal leukoencephalitis, is a rare and usually fatal viral disease of the central nervous system most frequently occurring in setting of immunodeficiency (HIV, intensive chemotherapy, organ and bone marrow transplantation and MS. PML is a demyelinating disease characterized by progressive damage or inflammation of the white matter of the brain at multiple locations. PML is caused by the human polyomavirus JC virus, which infects myelin-producing oligodendrocytes. The polyomavirus is called the JC virus (JCV), after the initials of the patient in whom it was first discovered. The virus is widespread, with 86% of the general population presenting antibodies, but it usually remains latent, causing disease only when the immune system has been severely weakened.

About 2-5% of AIDS patients develop PML. It is unclear why PML occurs more frequently in AIDS than in other immunosuppressive conditions; some research suggests that the effects of HIV on brain tissue, or on JCV itself, make JCV more likely to become active in the brain and increase its damaging inflammatory effects.

PML affects the white matter, which is mostly composed of axons from the outermost parts of the brain (cortex). Symptoms include weakness or paralysis, vision loss, impaired speech, and cognitive deterioration. PML destroys oligodendrocytes and produces intranuclear inclusions. PML is similar to another demyelinating disease, multiple sclerosis, but since it destroys the cells that produce myelin (unlike MS, in which myelin itself is attacked but can be replaced), it progresses much more quickly. The median survival of patients with PML as a complication of AIDS is 6 months. In 10% of patients, survival exceeds 12 months. The longest reported survival is 92 months from the onset of illness.

There are no approved therapies for PML and there is no known cure. In some cases, the disease slows or stops if the patient's immune system improves; some AIDS patients with PML have been able to survive for several years, with the advent of highly active antiretroviral therapy (HAART).

AIDS patients who start HAART after being diagnosed with PML tend to have a slightly longer survival time than patients who were already on HAART and then develop PML.

Natalizumab is a humanized monoclonal antibody against leukocyte alpha integrins. This antibody is used in the treatment of MS and prevents leukocyte trafficking into the central nervous system. Treatment with natalizumab reduces leukocyte mediated destruction of CNS myelin, which reduces relapses and slows progression of disability due to MS. However, in February of 2005 natalizumab was voluntarily suspended from marketing based on three PML case reports. The drug was reintroduced in the United States and Europe in July of 2006 as monotherapy to treat relapsing MS with a Black Box Warning: Risk of PML 1:1000 patients. Since the reintroduction in July 2006, one PML case was reported in the U.S. while four were reported ex-U.S. Thus development of PML and the lack of treatment for this disease remains a problem for MS patients receiving natalizumab treatment.

Other antiviral agents that have been studied as possible treatments for PML include cidofovir and interleukin-2, but this research is still preliminary.

Cytarabine (also known as ARA-C), a chemotherapy drug used to treat certain cancers, has been prescribed on an experimental basis for a small number of non-AIDS PML patients. It is reported to have stabilized the neurological condition of a minority of these patients. One patient regained some cognitive function lost as a result of PML.

There is usually no significant humoral or cellular immune response to JCV which makes it difficult to diagnose PML. Although JCV appears to be present in about 80% of the adult population, PML generally only develops in connection with a weakening of the immune system. The increasing use of immuno-suppressive drugs and the increasing number of HIV-infected patients has led to a considerable increase in PML diseases in recent years.

The known methods of diagnosis for detecting a PML disease essentially comprise image forming methods such as CT (computer tomography) and MRI (magnetic resonance imaging) as well as immunocytochemical methods based on biopsies or autopsies. Recently PCR detection methods have increased in importance, virus DNA amplification from cerebrospinal fluid (CSF) yielding reliable and specific results (Weber et al., J. Infect. Dis. (1994), 1138-1141 and McGuire et al., Annals of Neurology 37 (1995), 395-399).

There remains a need for effective treatment for this disease. The present invention provides this and other advantages as described further herein.

BRIEF SUMMARY OF THE INVENTION

The invention provides a method for treating Progressive Multifocal Leukoencephalopathy (PML). The method comprises administering to a patient a population of T cells activated and expanded according to a method comprising, activating a population of T cells in vitro with an agent which stimulates a TCR/CD3 complex-associated signal in the T cells, wherein the agent is attached on a surface; and stimulating a CD28 accessory molecule on the surface of the T cells in vitro with a ligand that binds the CD28 accessory molecule on the surface of the T cells, wherein the ligand is attached on the same surface as the agent; the activating and stimulating steps thereby inducing proliferation of the T cells.

In one embodiment, the agent is selected from the group consisting of an anti-CD3 antibody, or antigen-binding fragment thereof, an anti-TCR antibody, or antigen-binding fragment thereof, a superantigen, an MHC-peptide tetramer, and an antigen in a form suitable to trigger a primary activation signal in the T cell when complexed with the TCR/CD3 complex.

In one embodiment, the ligand is selected from the group consisting of an anti-CD28 antibody, or antigen-binding fragment thereof, B7-1 or a CD28-binding fragment thereof, and B7-2 or a CD28-binding fragment thereof.

In one embodiment, the surface is selected from the group consisting of a bead, a lipid bilayer, a cell surface, and a tissue-culture dish.

In one embodiment, the activated and expanded T cells are administered intravenously to the patient.

In one embodiment, the cell surface is of a human cell line. Preferably, the cell line is K562.

In one embodiment, the cell is genetically modified to express a human Fcγ receptor. Preferably, the human Fcγ receptor comprises CD32 or CD64.

In one embodiment, the cell is further genetically modified to express a co-stimulatory molecule selected from the group consisting of CD80, CD86, 4-1BBL, OX40L, ICOS-L, ICAM, PD-L1 and PD-L2.

In one embodiment, the cell has been modified to express a cytokine. In one embodiment, the cytokine is selected from the group consisting of IL-2, GM-CSF, IL-4, TNF-α, and IFN-γ.

The invention also provides a method for treating Chronic Lymphocytic Leukemia (CLL). The method comprises administering to a patient a population of T cells activated and expanded according to a method comprising, activating a population of T cells in vitro with an agent which stimulates a TCR/CD3 complex-associated signal in the T cells, wherein the agent is attached on a surface; and stimulating a CD28 accessory molecule on the surface of the T cells in vitro with a ligand that binds the CD28 accessory molecule on the surface of the T cells, wherein the ligand is attached on the same surface as the agent; the activating and stimulating steps thereby inducing proliferation of the T cells.

The invention also provides a method for treating a patient at risk of having Progressive Multifocal Leukoencephalopathy (PML) wherein the patient has undergone therapy that raises the risk for the development of PML. The method comprises administering to a patient a population of T cells activated and expanded according to a method comprising, activating a population of T cells in vitro with an agent which stimulates a TCR/CD3 complex-associated signal in the T cells, wherein the agent is attached on a surface; and stimulating a CD28 accessory molecule on the surface of the T cells in vitro with a ligand that binds the CD28 accessory molecule on the surface of the T cells, wherein the ligand is attached on the same surface as the agent; the activating and stimulating steps thereby inducing proliferation of the T cells.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

DETAILED DESCRIPTION

Figure 1:
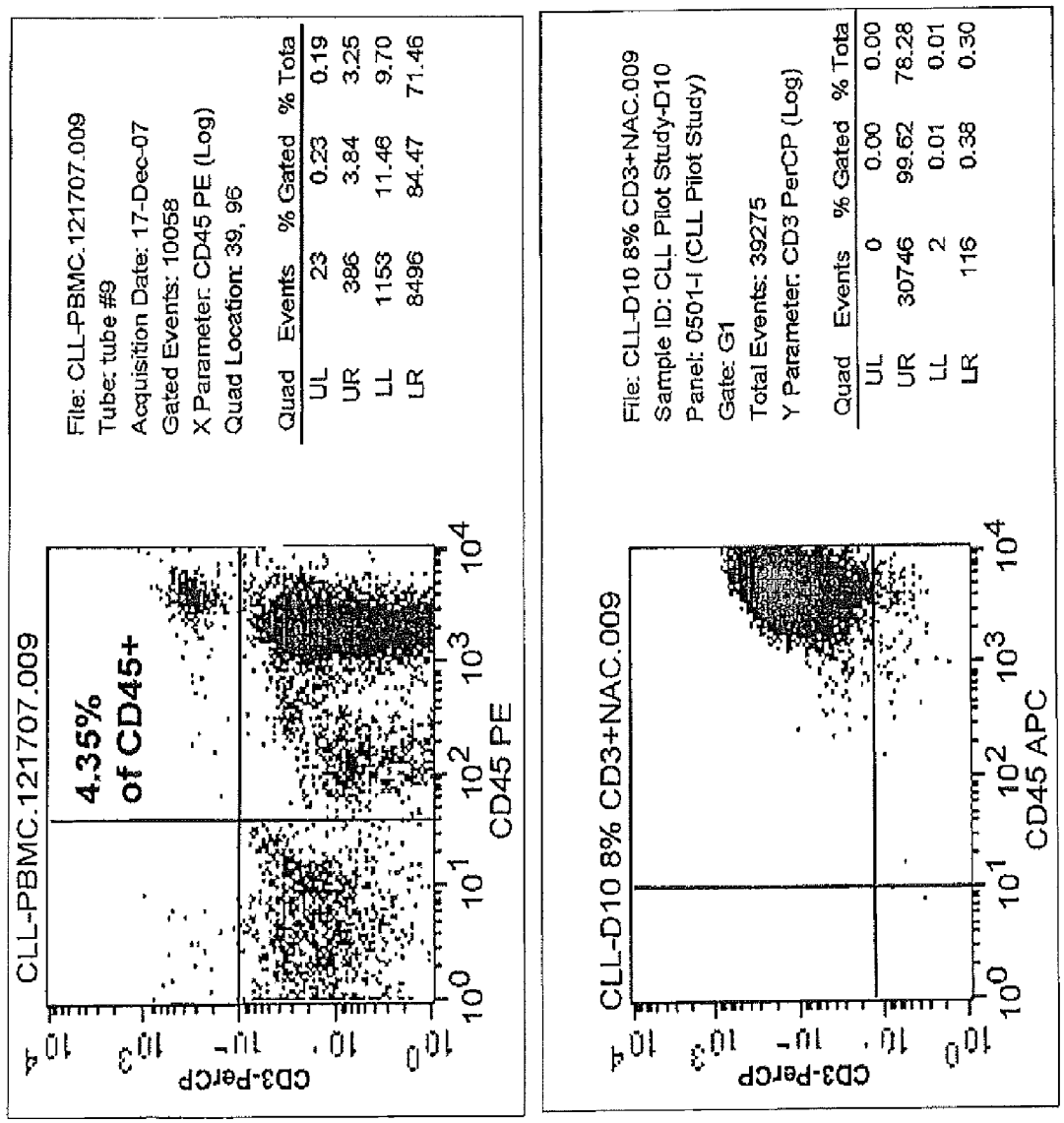
FIG. 1 is a dot plot showing CD45+/CD3+ T cells 10 days post anti-CD3/anti-CD28 stimulation from a CLL patient presenting with symptoms diagnostic of PML.

The present invention relates generally to the treatment of a patient having Progressive Multifocal Leukoencephalopathy (PML) or at risk of having PML using lymphocyte infusion. In another embodiment, the invention relates generally to the treatment of a patient having Chronic Lymphocytic Leukemia (CLL) or at risk of having CLL using lymphocyte infusion. Preferably, autologous lymphocyte infusion is used in the treatment. Autologous PBMCs are collected from a patient in need of treatment and T cells are activated and expanded using the methods described herein and known in the art and then infused back into the patient.

In yet another embodiment, the invention relates generally to the treatment of a patient at risk of developing PML or CLL. For example, treating a malignancy or an autoimmune disease in which chemotherapy and/or immunotherapy in a patient results in significant immunosuppression in the patient that raises the risk of the patient of developing PML or CLL.

One aspect of the invention provides a method of treating PML comprising administering to a patient a population of T cells activated and expanded according to a method comprising, (a) activating a population of T cells in vitro with an agent which stimulates a TCR/CD3 complex-associated signal in the T cells, wherein the agent is attached on a surface; and (b) stimulating a CD28 accessory molecule on the surface of the T cells in vitro with a ligand that binds the CD28 accessory molecule on the surface of the T cells, wherein the ligand is attached on the same surface as the agent; the activating and stimulating steps thereby inducing proliferation of the T cells. In this regard, illustrative agents include an anti-CD3 antibody, or antigen-binding fragment thereof, an anti-TCR antibody, or antigen-binding fragment thereof, a superantigen, an MHC-peptide tetramer, and an antigen in a form suitable to trigger a primary activation signal in the T cell when complexed with the TCR/CD3 complex. Illustrative ligands of the invention include, but are not limited to, an anti-CD28 antibody, or antigen-binding fragment thereof, B7-1 or a CD28-binding fragment thereof, and B7-2 or a CD28-binding fragment thereof.

In one embodiment of the invention the surface is selected from the group consisting of a bead, a lipid bilayer, a cell surface, and a tissue-culture dish. In another embodiment, the activated and expanded T cells are administered to the patient intravenously. In a further embodiment of the invention, the activated and expanded T cells of the invention are administered in conjunction with other therapies, such as natalizumab or other acceptable treatments for PML.

In certain embodiments, autologous antigen-specific T cells may be used. In this regard, JCV-specific T cells can be expanded using one or more JCV proteins or epitopes thereof as antigen (see e.g., U.S. Pat. No. 6,238,859). In other embodiments, BKV-specific T cells can be expanded using one or more BKV proteins or epitopes thereof as antigen. These antigen-specific T cells may be used alone or in conjunction with polyclonal autologous T cells activated and expanded using anti-CD3/anti-CD28 beads or aAPC using the methods as described herein. The invention also encompasses an aAPC comprising a nucleic acid encoding an antigen of interest such as JC and/or BK virus peptides.

Definitions

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

An "amino acid" as used herein is meant to include both natural and synthetic amino acids, and both D and L amino acids. "Standard amino acid" means any of the twenty L-amino acids commonly found in naturally occurring peptides. "Nonstandard amino acid residues" means any amino acid, other than the standard amino acids, regardless of whether it is prepared synthetically or derived from a natural source. As used herein, "synthetic amino acid" also encompasses chemically modified amino acids, including but not limited to salts, amino acid derivatives (such as amides), and substitutions. Amino acids contained within the peptides, and particularly at the carboxy- or amino-terminus, can be modified by methylation, amidation, acetylation or substitution with other chemical groups which can change a peptide's circulating half life without adversely affecting activity of the peptide. Additionally, a disulfide linkage may be present or absent in the peptides.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and $F(ab)_2$, as well as single chain antibodies and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, New York; Houston et al., 1988, Proc. Natl. Acad. Sci. USA 85:5879-5883; Bird et al., 1988, Science 242:423-426).

The term "agent", "ligand", or "agent that binds a cell surface moiety", as used herein, refers to a molecule that binds to a defined population of cells. The agent may bind any cell surface moiety, such as a receptor, an antigenic determinant, or other binding site present on the target cell population. The agent may be a protein, peptide, antibody and antibody fragments thereof, fusion proteins, synthetic molecule, an organic molecule (e.g., a small molecule), a carbohydrate, or the like. Within the specification and in the context of T cell stimulation, antibodies and natural ligands are used as prototypical examples of such agents.

The terms "agent that binds a cell surface moiety" and "cell surface moiety", as used herein, are used in the context of a ligand/anti-ligand pair. Accordingly, these molecules should be viewed as a complementary/anti-complementary set of molecules that demonstrate specific binding, generally of relatively high affinity.

As used herein, the term "autologous" is meant to refer to any material derived from the same individual to which it is later to be re-introduced into the individual.

"Allogeneic" refers to a graft derived from a different animal of the same species.

"Xenogeneic" refers to a graft derived from an animal of a different species.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

A "coding region" of an mRNA molecule also consists of the nucleotide residues of the mRNA molecule which are matched with an anti-codon region of a transfer RNA molecule during translation of the mRNA molecule or which encode a stop codon. The coding region may thus include nucleotide residues corresponding to amino acid residues which are not present in the mature protein encoded by the mRNA molecule (e.g., amino acid residues in a protein export signal sequence).

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the noncoding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Effective amount" or "therapeutically effective amount" are used interchangeably herein, and refer to an amount of a compound, formulation, material, or composition, as described herein effective to achieve a particular biological result. Such results may include, but are not limited to, the inhibition of virus infection as determined by any means suitable in the art.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

As used herein, the term "fragment," as applied to a nucleic acid, refers to a subsequence of a larger nucleic acid. A "fragment" of a nucleic acid can be at least about 15 nucleotides in length; for example, at least about 50 nucleotides to about 100 nucleotides; at least about 100 to about 500 nucleotides, at least about 500 to about 1000 nucleotides, at least about 1000 nucleotides to about 1500 nucleotides; or about 1500 nucleotides to about 2500 nucleotides; or about 2500 nucleotides (and any integer value in between).

As used herein, the term "fragment," as applied to a protein or peptide, refers to a subsequence of a larger protein or peptide. A "fragment" of a protein or peptide can be at least about 20 amino acids in length; for example at least about 50 amino acids in length; at least about 100 amino acids in length, at least about 200 amino acids in length, at least about 300 amino acids in length, and at least about 400 amino acids in length (and any integer value in between).

"Homologous" as used herein, refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous. By way of example, the DNA sequences 5'-ATTGCC-3' and 5'-TATGGC-3' share 50% homology.

The term "immunoglobulin" or "Ig", as used herein is defined as a class of proteins, which function as antibodies. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most mammals. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

An "isolated nucleic acid" refers to a nucleic acid segment or fragment which has been separated from sequences which flank it in a naturally occurring state, i.e., a DNA fragment which has been removed from the sequences which are normally adjacent to the fragment, i.e., the sequences adjacent to the fragment in a genome in which it naturally occurs. The term also applies to nucleic acids which have been substantially purified from other components which naturally accompany the nucleic acid, i.e., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (i.e., as a cDNA or a genomic or cDNA fragment produced by PCR or restriction enzyme digestion) independent of other sequences. It also includes a recombinant DNA which is part of a hybrid gene encoding additional polypeptide sequence.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

As used herein, the term "modulate" is meant to refer to any change in biological state, i.e. increasing, decreasing, and the like.

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

"Parenteral" administration of an immunogenic composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide which encodes or specified by a gene, causes the gene product to be produced in a cell substantially only if the cell is a cell of the tissue type corresponding to the promoter.

The term "RNA" as used herein is defined as ribonucleic acid.

The term "recombinant DNA" as used herein is defined as DNA produced by joining pieces of DNA from different sources.

The term "recombinant polypeptide" as used herein is defined as a polypeptide produced by using recombinant DNA methods.

The term "subject" is intended to include living organisms in which an immune response can be elicited (e.g., mammals).

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

The term "therapeutic" as used herein means a treatment and/or prophylaxis. A therapeutic effect is obtained by suppression, remission, or eradication of a disease state.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The phrase "under transcriptional control" or "operatively linked" as used herein means that the promoter is in the correct location and orientation in relation to a polynucleotide to control the initiation of transcription by RNA polymerase and expression of the polynucleotide.

"Variant" as the term is used herein, is a nucleic acid sequence or a peptide sequence that differs in sequence from a reference nucleic acid sequence or peptide sequence respectively, but retains essential properties of the reference molecule. Changes in the sequence of a nucleic acid variant may not alter the amino acid sequence of a peptide encoded by the reference nucleic acid, or may result in amino acid substitutions, additions, deletions, fusions and truncations. Changes in the sequence of peptide variants are typically limited or conservative, so that the sequences of the reference peptide and the variant are closely similar overall and, in many regions, identical. A variant and reference peptide can differ in amino acid sequence by one or more substitutions, additions, deletions in any combination. A variant of a nucleic acid or peptide can be a naturally occurring such as an allelic variant, or can be a variant that is not known to occur naturally. Non-naturally occurring variants of nucleic acids and peptides may be made by mutagenesis techniques or by direct synthesis.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-β, and/or reorganization of cytoskeletal structures, and the like.

"Activation", as used herein, refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division.

By the term "specifically binds," as used herein, is meant an antibody, or a ligand, which recognizes and binds with a cognate binding partner (e.g., a stimulatory and/or costimulatory molecule present on a T cell) protein present in a sample, but which antibody or ligand does not substantially recognize or bind other molecules in the sample.

A "stimulatory ligand," as used herein, means a ligand that when present on an antigen presenting cell (e.g., an aAPC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

A "stimulatory molecule," as the term is used herein, means a molecule on a T cell that specifically binds with a cognate stimulatory ligand present on an antigen presenting cell (e.g., an aAPC of the invention, among others).

"Loaded" with a peptide, as used herein, refers to presentation of an antigen in the context of an MHC molecule. "Loaded" as used herein also means the binding of an antibody to an Fc binding receptor on a cell, such as CD32 and/or CD64.

A "co-stimulatory signal", as used herein, refers to a signal, which in combination with a primary signal, such as TCR/CD3 ligation, leads to T cell proliferation and/or upregulation or downregulation of key molecules.

A "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to CD28, an MHC class I molecule, BTLA and a Toll ligand receptor.

"Co-stimulatory ligand," as the term is used herein, includes a molecule on an antigen presenting cell (e.g., an aAPC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation, activation, differentiation, and the like. A co-stimulatory ligand can include, but is not limited to, CD7, B7-1 (CD80), B7-2 (CD86), PD-L1, PD-L2, 4-1BBL, OX40L, inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds with CD83.

Description

The present invention provides a method of treating among other diseases, Chronic Lymphocytic Leukemia (CLL) and Progressive Multifocal Leukocephalopathy (PML) or any malignancy or autoimmune disease in which chemotherapy and/or immunotherapy results in significant immunosuppression that raises the risk for the development of PML. In one embodiment, the invention provides a method of using Fludarabine-Cyclophosphamide followed by adoptive transfer of CD3/CD28 ex vivo costimulated T cells for treating CLL and PML.

Sources of T Cells

Prior to expansion, a source of T cells is obtained from a subject. The term "subject" is intended to include living organisms in which an immune response can be elicited (e.g., mammals). Examples of subjects include humans, dogs, cats, mice, rats, and transgenic species thereof. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available in the art, may be used. In certain embodiments of the present invention, T cells can be obtained from a unit of blood collected from a subject using any number of techniques known to the skilled artisan, such as ficoll separation. In one preferred embodiment, cells from the circulating blood of an individual are obtained by apheresis or leukapheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. Again, surprisingly, initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, Ca-free, Mg-free PBS, PlasmaLyte A, or other saline solution with or without buffer. Alternatively, the undesirable components of the apheresis sample may be removed and the cells directly resuspended in culture media.

In another embodiment, T cells are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as $CD28^+$, $CD4^+$, $CD8^+$, $CD45RA^+$, and $CD45RO^+$T cells, can be further isolated by positive or negative selection techniques. For example, in one embodiment, T cells are isolated by incubation with anti-CD3/anti-CD28 (i.e., 3×28)-conjugated beads, such as DYNABEADS® M-450 CD3/CD28 T, for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used in the context of this invention. In certain embodiments, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for $CD4^+$ cells by negative selection, a monoclonal antibody cocktail typically includes antibodies to CD14, CD20, CD11b, CD16, HLA-DR, and CD8. In certain embodiments, it may be desirable to enrich for or positively select for regulatory T cells which typically express $CD4^+$, $CD25^+$, $CD62L^{hi}$, $GITR^+$, and $FoxP3^+$. Alternatively, in certain embodiments, T regulatory cells are depleted by anti-C25 conjugated beads or other similar method of selection.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc.). Such populations of cells may have therapeutic value and would be desirable to obtain. For example, using high concentration of cells allows more efficient selection of $CD8^+$ T cells that normally have weaker CD28 expression.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, $CD4^+$ T cells express higher levels of CD28 and are more efficiently captured than $CD8^+$ T cells in dilute concentrations. In one embodiment, the concentration of cells used is $5\times10^6$/ml. In other embodiments, the concentration used can be from about $1\times10^5$/ml to $1\times10^6$/ml, and any integer value in between.

In other embodiments, the cells may be incubated on a rotator for varying lengths of time at varying speeds at either 2-10° C. or at room temperature.

If desired or necessary, monocyte populations (i.e., $CD14^+$ cells) may be depleted from blood preparations prior to ex vivo expansion by a variety of methodologies, including anti-CD14 coated beads or columns, or utilization of the phagocytic activity of these cells to facilitate removal, or by the use of counterflow centrifugal elutriation. Accordingly, in one embodiment, the invention uses paramagnetic particles of a size sufficient to be engulfed by phagocytotic monocytes. In certain embodiments, the paramagnetic particles are commercially available beads, for example, those produced by Dynal AS under the trade name Dynabeads™. Exemplary Dynabeads™ in this regard are M-280, M-450, and M-500. In one aspect, other non-specific cells are removed by coating the paramagnetic particles with "irrelevant" proteins (e.g., serum proteins or antibodies). Irrelevant proteins and antibodies include those proteins and antibodies or fragments thereof that do not specifically target the T cells to be expanded. In certain embodiments the irrelevant beads include beads coated with sheep anti-mouse antibodies, goat anti-mouse antibodies, and human serum albumin.

In brief, such depletion of monocytes is performed by preincubating PBMC isolated from whole blood or apheresed peripheral blood with one or more varieties of irrelevant or non-antibody coupled paramagnetic particles at any amount that allows for removal of monocytes (approximately a 20:1 bead:cell ratio) for about 30 minutes to 2 hours at 22 to 37 degrees C., followed by magnetic removal of cells which have attached to or engulfed the paramagnetic particles. Such separation can be performed using standard methods available in the art. For example, any magnetic separation methodology may be used including a variety of which are commercially available, (e.g., DYNAL® Magnetic Particle Concentrator (DYNAL MPC®)). Assurance of requisite depletion can be monitored by a variety of methodologies known to those of ordinary skill in the art, including flow cytometric analysis of CD14 positive cells, before and after said depletion.

T cells for stimulation can also be frozen after the washing step, which does not require the monocyte-removal step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and Plasma-Lyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In certain embodiments, cryopreserved cells are thawed and washed as described herein and allowed to rest for one hour at room temperature prior to activation using the methods of the present invention.

Also contemplated in the context of the invention is the collection of blood samples or leukapheresis product from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In one embodiment a blood sample or a leukapheresis is taken from a generally healthy subject. In certain embodiments, a blood sample or a leukapheresis is taken from a generally healthy subject who is at risk of developing a disease, but who has not yet developed a disease, and the cells of interest are isolated and frozen for later use. In certain embodiments, the T cells may be expanded, frozen, and used at a later time. In certain embodiments, samples are collected from a patient shortly after diagnosis of a particular disease as described herein but prior to any treatments. In a further embodiment, the cells are isolated from a blood sample or a leukapheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxin, fludaribine, cyclosporin, FK506, rapamycin, mycophenolic acid, steroids, FR901228, and irradiation. These drugs inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun. 73:316-321, 1991; Bierer et al., Curr. Opin. Immun 5:763-773, 1993; Isoniemi (supra)). In a further embodiment, the cells are isolated for a patient and frozen for later use in conjunction with (e.g., before, simultaneously or following) bone marrow or stem cell transplantation, T cell ablative therapy using either chemotherapy agents such as, fludarabine, external-beam radiation therapy (XRT), cyclophosphamide, or antibodies such as OKT3 or CAMPATH. In another embodiment, the cells are isolated prior to and can be frozen for later use for treatment following B-cell ablative therapy such as agents that react with CD20, e.g., Rituxan.

In a further embodiment of the present invention, T cells are obtained from a patient directly following treatment. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T cells, dendritic cells, or other cells of the hematopoetic lineage, during this recovery phase. Further, in certain embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

Activation and Expansion of T Cells

T cells are activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, the T cells of the invention are expanded by contact with a surface having attached thereto an agent that stimulates a CD3/TCR complex associated signal and a ligand that stimulates a co-stimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either $CD4^+$ T cells or $CD8^+$ T cells, an anti-CD3 antibody and an anti-CD28 antibody. Examples of an anti-CD28 antibody include 9.3, B-T3, XR-CD28 (Diaclone, Besançon, France) can be used as can other methods commonly known in the art (Berg et al., *Transplant Proc.* 30(8):

3975-3977, 1998; Haanen et al., *J. Exp. Med.* 190(9):13191328, 1999; Garland et al., *J. Immunol Meth.* 227(1-2):53-63, 1999).

In certain embodiments, the primary stimulatory signal and the co-stimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one embodiment, the agent providing the co-stimulatory signal is bound to a cell surface and the agent providing the primary activation signal is in solution or coupled to a surface. In certain embodiments, both agents can be in solution. In another embodiment, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial APCs that are contemplated for use in activating and expanding T cells in the present invention.

The invention encompasses an aAPC wherein the co-stimulatory ligand is a cognate binding partner that specifically binds with a co-stimulatory molecule, as well as where the ligand is an antibody that specifically binds with a costimulatory molecule, and any combination thereof, such that a single aAPC can comprise both nucleic acids encoding costimulatory ligands and/or antibodies specific for costimulatory molecules present on the T cell, and any combination thereof. The extensive disclosure regarding aAPCs provided in WO 03/057171 and US2003/0147869 is incorporated by reference as if set forth in its entirety herein.

In one embodiment, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the co-stimulatory signal is an anti-CD28 antibody or antigen-binding fragment thereof; and both agents are co-immobilized to the same bead in equivalent molecular amounts. In one embodiment, a 1:1 ratio of each antibody bound to the beads for CD4+ T cell expansion and T cell growth is used. In certain aspects of the present invention, a ratio of anti CD3:CD28 antibodies bound to the beads is used such that an increase in T cell expansion is observed as compared to the expansion observed using a ratio of 1:1. In one particular embodiment an increase of from about 0.5 to about 3 fold is observed as compared to the expansion observed using a ratio of 1:1. In one embodiment, the ratio of CD3:CD28 antibody bound to the beads ranges from 100:1 to 1:100 and all integer values there between. In one aspect of the present invention, more anti-CD28 antibody is bound to the particles than anti-CD3 antibody, i.e., the ratio of CD3:CD28 is less than one. In certain embodiments of the invention, the ratio of anti CD28 antibody to anti CD3 antibody bound to the beads is greater than 2:1. In one particular embodiment, a 1:100 CD3:CD28 ratio of antibody bound to beads is used. In another embodiment, a 1:75 CD3:CD28 ratio of antibody bound to beads is used. In a further embodiment, a 1:50 CD3:CD28 ratio of antibody bound to beads is used. In another embodiment, a 1:30 CD3:CD28 ratio of antibody bound to beads is used. In one preferred embodiment, a 1:10 CD3:CD28 ratio of antibody bound to beads is used. In another embodiment, a 1:3 CD3:CD28 ratio of antibody bound to the beads is used. In yet another embodiment, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particle to cells may be dependant on particle size relative to the target cell. For example, small sized beads could only bind a few cells, while larger beads could bind many. In certain embodiments the ratio of cells to particles ranges from 1:100 to 100:1 and any integer values in-between and in further embodiments the ratio comprises 1:9 to 9:1 and any integer values in between, can also be used to stimulate T cells. The ratio of anti-CD3- and anti-CD28-coupled particles to T cells that result in T cell stimulation can vary as noted above, however certain preferred values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one preferred ratio being at least 1:1 particles per T cell. In one embodiment, a ratio of particles to cells of 1:1 or less is used. In one particular embodiment, a preferred particle: cell ratio is 1:5. In further embodiments, the ratio of particles to cells can be varied depending on the day of stimulation. For example, in one embodiment, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular embodiment, the ratio of particles to cells is 1:1 on the first day of stimulation and adjusted to 1:5 on the third and fifth days of stimulation. In another embodiment, particles are added on a daily or every other day basis to a final ratio of 1:1 on the first day, and 1:5 on the third and fifth days of stimulation. In another embodiment, the ratio of particles to cells is 2:1 on the first day of stimulation and adjusted to 1:10 on the third and fifth days of stimulation. In another embodiment, particles are added on a daily or every other day basis to a final ratio of 1:1 on the first day, and 1:10 on the third and fifth days of stimulation. One of skill in the art will appreciate that a variety of other ratios may be suitable for use in the present invention. In particular, ratios will vary depending on particle size and on cell size and type.

Using certain methodologies it may be advantageous to maintain long-term stimulation of a population of T cells following the initial activation and stimulation, by separating the T cells from the stimulus after a period of about 7 to about 14 days. The rate of T cell proliferation is monitored periodically (e.g., daily) by, for example, examining the size or measuring the volume of the T cells, such as with a Coulter Counter. In this regard, a resting T cell has a mean diameter of about 6.8 microns, and upon initial activation and stimulation, in the presence of the stimulating ligand, the T cell mean diameter will increase to over 12 microns by day 4 and begin to decrease by about day 6. When the mean T cell diameter decreases to approximately 8 microns, the T cells may be reactivated and re-stimulated to induce further proliferation of the T cells. Alternatively, the rate of T cell proliferation and time for T cell re-stimulation can be monitored by assaying for the presence of cell surface molecules, such as, CD154, CD54, CD25, CD137, CD134, which are induced on activated T cells.

In one embodiment, T cell stimulation is performed with anti-CD3 and anti-CD28 antibodies co-immobilized on beads (3×28 beads), for a period of time sufficient for the cells to return to a quiescent state (low or no proliferation) (approximately 8-14 days after initial stimulation). The stimulation signal is then removed from the cells and the cells are washed and infused back into the patient. The cells at the end of the stimulation phase are rendered "super-inducible" by the methods of the present invention, as demonstrated by their ability to respond to antigens and the ability of these cells to demonstrate a memory-like phenotype, as is evidence by the examples. Accordingly, upon re-stimulation either exogenously or by an antigen in vivo after infusion, the activated T cells demonstrate a robust response characterized by unique phenotypic properties, such as sustained CD 154 expression and increased cytokine production.

In further embodiments of the present invention, the cells, such as T cells, are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In one embodiment the cells (for example, $10^4$ to $10^9$ T cells) and beads (for example, DYNABEADS® M-450 CD3/CD28 T paramagnetic beads at a ratio of 1:1) are combined in a buffer, preferably PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present invention. In certain embodiments, it may be desirable to significantly decrease the volume in which particles and cells are mixed together (i.e., increase the concentration of cells), to ensure maximum contact of cells and particles. For example, in one embodiment, a concentration of about 2 billion cells/ml is used. In another embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain embodiments. For example, using high concentration of cells allows more efficient selection of CD8+ T cells that normally have weaker CD28 expression.

In a related embodiment, it may be desirable to use lower concentrations of cells. By significantly diluting the mixture of T cells and particles, interactions between particles and cells is minimized. This selects for cells that express high amounts of desired antigens to be bound to the particles. For example, CD4+ T cells express higher levels of CD28 and are more efficiently captured and stimulated than CD8+ T cells in dilute concentrations. In one embodiment, the concentration of cells used is about $5\times10^6$/ml. In other embodiments, the concentration used can be from about $1\times10^5$/ml to about $1\times10^6$/ml, and any integer value in between.

The buffer that the cells are suspended in may be any that is appropriate for the particular cell type. When utilizing certain cell types the buffer may contain other components, e.g., 0.5-10% serum, necessary to maintain cell integrity during the process. In another embodiment, the cells and beads may be combined in cell culture media. The cells and beads may be mixed, for example, by rotation, agitation or any means for mixing, for a period of time ranging from one minute to several hours. The container of beads and cells is then concentrated by a force, such as placing in a magnetic field. Media and unbound cells are removed and the cells attached to the beads are washed, for example, by pumping via a peristaltic pump, and then resuspended in media appropriate for cell culture.

In one embodiment of the present invention, the mixture may be cultured for several hours (about 3 hours) to about 14 days or any hourly integer value in between. In another embodiment, the mixture may be cultured for 21 days. In one embodiment of the invention the beads and the T cells are cultured together for about eight days. In another embodiment, the beads and T cells are cultured together for 2-3 days. Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFβ, and TNF-α. or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

When using a magnetic field as the concentrating force the magnetic field strength applied to the cells prior to cell culture may be between the range of 200 gauss to 12,000 gauss on the magnetic surface. The shape and size of the magnet may be adapted to the size and shape of the mixing or cell culture vessels or to any other parameter that facilitates or increases cell to cell contact and concentration of the cells. The magnetic force may be diffused by placing a material that acts as a buffer or spacer between the magnet and the paramagnetic beads contained within the mixture with cells. A strong magnetic force is generally considered to be at least 7500 gauss at the surface, whereas a weak magnetic force is considered to be in the range of 2000-2500 gauss at the surface. The approximate magnetic force applied by a magnet on a paramagnetic bead depends upon the volume of the paramagnetic bead and the magnetic field strength according to the following formula:

$$F_{mag}=(v)(\Psi)(B)(dB/dx)$$

where $F_{mag}$ equals the magnetic force, v equals the volume of the paramagnetic bead, $\Psi$ equals the magnetic susceptibility of a paramagnetic bead (a value provided by the manufacturer), B equals the magnetic field strength, and (dB/dx) equals the field strength gradient. One of skill in the art will appreciate that the factors on the right-hand side of the equation can be obtained or measured, allowing the magnetic force applied to be calculated.

Cells stimulated by the methods of the present invention are activated as shown by the induction of signal transduction, expression of cell surface markers and/or proliferation. One such marker appropriate for T cells is CD154 which is an important immunomodulating molecule. The expression of CD154 is extremely beneficial in amplifying the immune response. CD154 interacts with the CD40 molecule expressed on many B cells, dendritic cells, monocytes, and some endothelial cells. Accordingly, this unexpected and surprising increase in CD154 expression is likely to lead to more efficacious T cell compositions. Stimulation of CD3+ cells as described herein provides T cells that express a 1.1 to 20-fold increases in the levels of certain cell surface markers such as CD154 expression on days 1, 2, 3, or 4 following stimulation. (See e.g., US Patent Application Publication 2006-0121005). Expression of another cell surface marker, CD25, also was greater on T cells after concentration and stimulation than on cells prior to culture or cells stimulated by other methods.

The agent/ligand-coated surfaces, such as, beads may be separated from the cells prior to culture, at any point during culture, or at the termination of culture. In addition, the agent-coated surfaces ligated to the target cells may be separated from the non-binding cells prior to culture or the other cells may remain in culture as well. In one embodiment, prior to culture, the agent-coated beads and target cells are not separated but are cultured together. In a further embodiment, the beads and target cells are first concentrated by application of a force, resulting in cell surface protein ligation, thereby inducing stimulation and subsequent activation.

Also contemplated by this invention, are other means to increase the concentration of the target cells, for example, a T cell fraction bound to a surface coated with primary and secondary stimulatory molecules. In addition to application of a magnetic force, other forces greater than gravitational force may be applied, for example, but not limited to, centrifugal force, transmembrane pressure, and a hydraulic force. Concentration may also be accomplished by filtration.

One of skill in the art will readily appreciate that contact between the agent-coated beads and the cells to be stimulated can be increased by concentration using other forces. Accordingly, any means for concentrating cells with cell surface protein binding ligands will be sufficient as long as the concentration brings together cells and agents in a manner that exceeds gravity or diffusion.

It should be understood that in various embodiments the agent-coated surface may be a particle, such as a bead which is mixed with the cells and concentrated in a small volume in a magnetic field, thus drawing all the particles and particle bound cells into a defined and concentrated area. In certain embodiments, the agent-coated surface may be drawn together by force within thirty seconds to four hours of being exposed to the target cells. In other embodiments the time may be from 1 minute to 2 hours, or all integer ranges in between. Application of a force to a cell population with receptor bearing cells that is mixed with a surface to which at least one cell surface ligand is attached may induce cell receptor polarization, aggregating cell surface molecules. This means for inducing cell surface polarization may enhance signaling within the cell by aggregating cell surface molecules that comprise lipid rafts. Such aggregation can induce a signal pathway, which may lead to down-regulation or suppression of a cellular event. Alternatively, the aggregation of cell surface molecules may lead to up-regulation or activation of a cellular event.

A cellular event may include, for example, receptor-mediated signal transduction that induces or suppresses a particular pathway, including an apoptotic pathway, or induces phosphorylation of proteins, or stimulates or suppresses growth signals. In one embodiment, the cells may be lymphocytes, particularly a T cell, and the cell surface ligand may be an anti-CD3 antibody attached to a surface, for example, a particle. The particle may be a paramagnetic bead and the force applied a magnetic force. Application of a magnetic force to a mixture of the lymphocytes and anti-CD3-coated surface of the paramagnetic bead may cause the CD3 receptors of the T cell to polarize more quickly than would occur in the absence of an external force. This method of stimulating the T cell promotes more rapid activation of the T cell immune response pathways and proliferation of cells.

In one embodiment of the present invention, bead:cell ratios can be tailored to obtain a desired T cell phenotype. In one particular embodiment, bead:cell ratios can be varied to selectively expand or delete antigen-specific (memory) T cells. In one embodiment, the particular bead:cell ratio used selectively deletes antigen-specific T cells. In a further embodiment, the particular bead:cell ratio used selectively expands antigen-specific T cells. The skilled artisan would readily appreciate that any ratio can be used as long as the desired expansion or deletion of antigen-specific T cells occurs. Therefore, the compositions and methods described herein can be used to expand specific populations of T cells, or to delete specific populations of T cells, for use in any variety of immunotherapeutic settings described herein.

In another embodiment, the time of exposure to stimulatory agents such as anti-CD3/anti-CD28 (i.e., 3×28)-coated beads may be modified or tailored to obtain a desired T cell phenotype. Alternatively, a desired population of T cells can be selected using any number of selection techniques, prior to stimulation. One may desire a greater population of helper T cells ($T_H$), typically CD4+ as opposed to CD830 cytotoxic or regulatory T cells, because an expansion of $T_H$ cells could improve or restore overall immune responsiveness. While many specific immune responses are mediated by CD8+ antigen-specific T cells, which can directly lyse or kill target cells, most immune responses require the help of CD4+ T cells, which express important immune-regulatory molecules, such as GM-CSF, CD40L, and IL-2, for example. Where CD4-mediated help if preferred, a method, such as that described herein, which preserves or enhances the CD4: CD8 ratio could be of significant benefit. Increased numbers of CD4+ T cells can increase the amount of cell-expressed CD40L introduced into patients, potentially improving target cell visibility (improved APC function). Similar effects can be seen by increasing the number of infused cells expressing GM-CSF, or IL-2, all of which are expressed predominantly by CD4+ T cells. Alternatively, in situations where CD4-help is needed less and increased numbers of CD8+ T cells are desirous, the approaches described herein can also be utilized, by for example, pre-selecting for CD8+ cells prior to stimulation and/or culture. Such situations may exist where increased levels of IFN-γ or increased cytolysis of a target cell is preferred. In a further embodiment, the processes described herein can be modified or tailored to promote homing of T cells to particular sites of interest, such as lymph nodes or sites of inflammation, or to bone marrow, for example.

Additionally, in certain embodiments, it may be desirable to negatively select T regulatory cells to remove them from the culture. Classically, T regulatory cells have a CD4+, CD25+, CD62L$^{hi}$, GITR+, and FoxP3+ phenotype (see for example, Woo, et al., J Immunol. 2002 May 1; 168(9):4272-6; Shevach, E. M., Annu. Rev. Immunol. 2000, 18:423; Stephens, et al., Eur. J. Immunol. 2001, 31:1247; Salomon, et al., Immunity 2000, 12:431; and Sakaguchi, et al., Immunol. Rev. 2001, 182:18). In certain embodiments, regulatory T cells can also be generated and expanded using the methods of the present invention. The regulatory T cells can be antigen-specific and/or polyclonal. Regulatory T cells can also be generated using art-recognized techniques as described for example, in Woo, et al.; Shevach, E. M.; Stephens, et al.; Salomon, et al.; and Sakaguchi, et al.; Supra. To effectuate isolation of different T cell populations, exposure times to the particles may be varied. For example, in one embodiment, T cells are isolated by incubation with 3×28 beads, such as Dynabeads M-450, for a time period sufficient for positive selection of the desired T cells. In one embodiment, the time period is about 30 minutes. In a further embodiment, the time period is at least 1, 2, 3, 4, 5, or 6 hours. In yet another embodiment, the time period is 10 to 24 hours or more. In one particular embodiment, the incubation time period is 24 hours. For isolation of T cells from cancer patients, use of longer incubation times, such as 24 hours, can increase cell yield.

To effectuate isolation of different T cell populations, exposure times to the concentration force may be varied or pulsed. For example when such force is a magnet, exposure to the magnet or the magnetic field strength may be varied, and/or expansion times may be varied to obtain the specific phenotype of interest. The expression of a variety of phenotypic markers change over time; therefore, a particular time point may be chosen to obtain a specific population of T cells. Accordingly, depending on the cell type to be stimulated, the stimulation and/or expansion time may be 10 weeks or less, 8 weeks or less, four weeks or less, 2 weeks or less, 10 days or less, or 8 days or less (four weeks or less includes all time ranges from 4 weeks down to 1 day (24 hours) or any value between these numbers). In some embodiments in may be desirable to clone T cells using, for example, limiting dilution or cell sorting, wherein longer stimulation time may be necessary. In some embodiments, stimulation and expansion may be carried out for 6 days or less, 4 days or less, 2 days or less, and in other embodiments for as little as 24 or less hours, and preferably 4-6 hours or less (these ranges include any integer values in between). When stimulation of T cells is carried out for shorter periods of time, the population of T cells may not increase in number as dramatically, but the population will provide more robust and healthy activated T cells that can continue to proliferate in vivo and more closely resemble the natural effector T cell pool. As the availability of T cell help is often the limiting factor in antibody responses to protein antigens, the ability to selectively expand or selectively infuse a CD4$^+$ rich population of T cells into a subject is extremely beneficial. Further benefits of such enriched populations are readily apparent in that activated helper T cells that recognize antigens presented by B lymphocytes deliver two types of stimuli, physical contact and cytokine production, that result in the proliferation and differentiation of B cells.

T cells that have been exposed to varied stimulation times may exhibit different characteristics. For example, typical blood or apheresed peripheral blood mononuclear cell products have a helper T cell population ($T_H$, CD4$^+$) that is greater than the cytotoxic or suppressor T cell population ($T_C$, CD8). Ex vivo expansion of T cells by stimulating CD3 and CD28 receptors produces a population of T cells that prior to about days 8-9 consists predominately of $T_H$ cells, while after about days 8-9, the population of T cells comprises an increasingly greater population of $T_C$ cells. Accordingly, depending on the purpose of treatment, infusing a subject with a T cell population comprising predominately of $T_H$ cells may be advantageous. Similarly, if an antigen-specific subset of $T_C$ cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

In one such example, among the important phenotypic markers that reproducibly vary with time are the high affinity IL-2 receptor (CD25), CD40 ligand (CD154), and CD45RO (a molecule that by preferential association with the TCR may increase the sensitivity of the TCR to antigen binding). As one of ordinary skill in the art readily appreciates, such molecules are important for a variety of reasons. For example, CD25 constitutes an important part of the autocrine loop that allows rapid T cell division. CD154 has been shown to play a key role in stimulating maturation of the antigen-presenting dendritic cells; activating B-cells for antibody production; regulating $T_H$ cell proliferation; enhancing $T_C$ cell differentiation; regulating cytokine secretion of both $T_H$ cells and antigen-presenting cells; and stimulating expression of co-stimulatory ligands, including CD80, CD86, and CD154.

Cytokine and chemokine production peaks in the first few days of the ex vivo expansion process. Accordingly, because cytokines are known to be important for mediating T cell activation and function as well as immune response modulation, such cytokines are likely critical in the development of a therapeutic T cell product, that is able to undergo reactivation upon contact with an additional antigen challenge. Cytokines and chemokines important in this regard, include, but are not limited to, IL-2, IL-4, TNF-α, and IFN-γ, MIP-1α, MIP-1β, and RANTES. Thus, by obtaining a population of T cells during the first few days of expansion and infusing these cells into a subject, a therapeutic benefit may occur in which additional activation and expansion of T cells in vivo occurs.

In addition to the cytokines and the markers discussed previously, expression of adhesion molecules known to be important for mediation of T cell activation and immune response modulation also change dramatically but reproducibly over the course of the ex vivo expansion process. For example, CD62L is important for homing of T cells to lymphoid tissues and trafficking T cells to sites of inflammation. Under certain circumstances of disease and injury, the presence of activated T cells at these sites may be disadvantageous. Because down-regulation of CD62L occurs early following activation, the T cells could be expanded for shorter periods of time. Conversely, longer periods of time in culture would generate a T cell population with higher levels of CD62L and thus a higher ability to target the activated T cells to these sites under other preferred conditions.

Another example of a polypeptide whose expression varies over time is CCR7. Naive T cells may also be distinguished by a relatively high level of expression of the chemokine receptor, CCR7 (CCR7$^{hi}$) as compared to the level of expression observed for non-naive T cells (see, e.g., McFarland et al., PNAS, Vol. 97(8), pp. 4215-4220 (2000); Ishimaru et al., Nature Immunol., Vol. 7(7), pp. 763-772 (2006); and Kern et al., Eur. J. Immunol., Vol. 29, pp. 2908-2915 (1999)). In contrast, memory cells, for example, may be characterized by a CD27$^{low}$, CD44$^{hi}$, CD45RA$^-$, CD45RO$^+$, CD57$^{+(or\ hi)}$, CD62L$^{low}$, and/or CCR7$^{low}$ phenotype (see, e.g., Kern et al., Eur. J. Immunol., Vol. 29, pp. 2908-2915 (1999), and Baccala et al., J. Immunol., Vol. 174:4606-4612 (2005)).

Another example of a polypeptide whose expression varies over time is CD49d, an adhesion molecule that is involved in trafficking lymphocytes from blood to tissues spaces at sites of inflammation. Binding of the CD49d ligand to CD49d also allows the T cell to receive co-stimulatory signals for activation and proliferation through binding by VCAM-1 or fibronectin ligands. The expression of the adhesion molecule CD54, involved in T cell-APC and T cell-T cell interactions as well as homing to sites of inflammation, also changes over the course of expansion. Accordingly, T cells could be stimulated for selected periods of time that coincide with the marker profile of interest and subsequently collected and infused. Thus, T cell populations could be tailored to express the markers believed to provide the most therapeutic benefit for the indication to be treated.

With respect to T cells, the T cell populations resulting from the various expansion methodologies described herein may have a variety of specific phenotypic properties, depending on the conditions employed. Such phenotypic properties include enhanced expression of CD25, CD154, IFN-γ and GM-CSF, as well as altered expression of CD137, CD134, CD62L, and CD49d. The ability to differentially control the expression of these moieties may be very important. For example, higher levels of surface expression of CD154 on "tailored T cells," through contact with CD40 molecules expressed on antigen-presenting cells (such as dendritic cells, monocytes, and even leukemic B cells or lymphomas), will enhance antigen presentation and immune function. Such strategies are currently being employed by various companies to ligate CD40 via antibodies or recombinant CD40L. The approach described herein permits this same signal to be delivered in a more physiological manner, e.g., by the T cell. The ability to increase IFN-γ secretion by tailoring the T cell activation process could help promote the generation of TH1-type immune responses, important for anti-tumor and anti-viral responses. Like CD154, increased expression of GM-CSF can serve to enhance APC function, particularly through its effect on promoting the maturation of APC progenitors into more functionally competent APC, such as dendritic cells. Altering the expression of CD137 and CD134 can affect a T cell's ability to resist or be susceptible to apoptotic signals. Controlling the expression of adhesion/homing receptors, such as CD62L and/or CD49d and/or CCR7 may determine the ability of infused T cells to home to lymphoid organs, sites of infection, or tumor sites.

An additional aspect of the present invention provides a T cell population or composition that has been depleted of CD8$^+$ or CD4$^+$ cells prior to expansion. In one embodiment, CD8$^+$ cells are depleted by antibodies directed to the CD8$^+$ marker. One of ordinary skill in the art would readily be able to identify a variety of particular methodologies for depleting a sample of CD8$^+$ or CD4$^+$ cells or conversely enriching the CD4$^+$ or CD8$^+$ cell content. With respect to enriching for CD4$^+$ cells, one aspect of the present invention is focused on the identification of an extremely robust CD154 expression profile upon stimulation of T cell populations wherein $T_C$ (CD8$^+$) cells have been depleted. As indicated above, CD154 is an important immunomodulating molecule whose expression is extremely beneficial in amplifying the immune response. Accordingly an increase in CD154 expression is likely to lead to more efficacious T cell compositions.

In certain embodiments, it is desirable to activate and expand autologous antigen-specific T cells. In this regard, antigen-specific T cells, such as JCV-specific T cells, can be expanded using one or more proteins or epitopes thereof as antigen, such as JCV proteins or epitopes thereof (see e.g., U.S. Pat. No. 6,238,859). In some embodiments, antigen-specific T cells, such as BKV-specific T cells, can be expanded using one or more proteins or epitopes thereof as antigen, such as BKV proteins or epitopes thereof. These antigen-specific T cells may be used alone or in conjunction with polyclonal autologous T cells activated and expanded using anti-CD3/anti-CD28 beads or aAPCs using the methods as described herein.

An additional aspect of the present invention provides a T cell population or composition that has been depleted or enriched for populations of cells expressing a variety of markers, such as CD62L, CD45RA or CD45RO, cytokines (e.g., IL-2, IFN-γ, IL-4, IL-10), cytokine receptors (e.g., CD25), perforin, adhesion molecules (e.g. VLA-1, VLA-2, VLA-4, LPAM-1, LFA-1), and/or homing molecules (e.g., L-Selectin), prior to expansion. In one embodiment, cells expressing any of these markers are depleted or positively selected by antibodies or other ligands/binding agents directed to the marker. One of ordinary skill in the art would readily be able to identify a variety of particular methodologies for depleting or positively selecting for a sample of cells expressing a desired marker.

The phenotypic properties of T cell populations of the present invention can be monitored by a variety of methods including standard flow cytometry methods and ELISA methods known by those skilled in the art.

In the various embodiments, one of ordinary skill in the art understands removal of the stimulation signal from the cells is dependent upon the type of surface used. For example, if paramagnetic beads are used, then magnetic separation is the feasible option. Separation techniques are described in detail by paramagnetic bead manufacturers' instructions (for example, DYNALBiotech, Oslo, Norway a unit of Invitrogen Life Technologies). Furthermore, filtration may be used if the surface is a bead large enough to be separated from the cells. In addition, a variety of transfusion filters are commercially available, including 20 micron and 80 micron transfusion filters (Baxter). Accordingly, so long as the beads are larger than the mesh size of the filter, such filtration is highly efficient. In a related embodiment, the beads may pass through the filter, but cells may remain, thus allowing separation. In one particular embodiment the biocompatible surface used degrades (i.e., biodegradable) in culture during the exposure period.

Those of ordinary skill in the art will readily appreciate that the cell stimulation methodologies described herein may be carried out in a variety of environments (i.e., containers). For example, such containers may be culture flasks, culture bags, or any container capable of holding cells, preferably in a sterile environment. In one embodiment of the present invention a bioreactor is also useful. For example, several manufacturers currently make devices that can be used to grow cells and be used in combination with the methods of the present invention. See for example, Celdyne Corp., Houston, Tex.; Unisyn Technologies, Hopkinton, Mass.; Synthecon, Inc., Houston, Tex.; Aastrom Biosciences, Inc., Ann Arbor, Mich.; Wave Biotech LLC, Bedminster, N.J. Further, patents covering such bioreactors include U.S. Pat. Nos. 6,096,532; 5,985,653; 5,888,807; 5,190,878, which are incorporated herein by reference.

In one embodiment, the magnet used for simultaneous stimulation and concentration of the cells of the present invention may be incorporated into the base rocker platform of a bioreactor device, such as "The Wave" (Wave Biotech LLC, Bedminster, N.J.). The magnet, or a magnetizable element, may also be enclosed into a standard bioreactor vessel such as a cylindrical application unit. This built-in magnetic element may be capable of being switched on and off as desired at various points in the cell culture procedure. The integrated magnet, or magnetizable element, is positioned so as to allow a magnetic field emanating therefrom to pass through the culture vessel. In certain embodiments, the magnet, or magnetizable element, is incorporated within a wall, or alternatively, within the body of the culture vessel. In a further embodiment, the cells can be magnetically concentrated and/or activated, magnetically separated or isolated at a desired point during culture without the need to transfer cells to a different culture or magnetic separation unit. Use of such a built-in magnetic element can facilitate culture, stimulation and concentration, and separation processes to enable expansion and tailoring of specific functional cell populations for immunotherapeutic infusion into patients in cell or gene-based therapies. Further, this device provides an improved means for specific production of molecules both inside cells and their secretion to the outside of cells.

The integrated magnetic or magnetizable device as described above can be used to either remove magnetic particles from the culture, retaining them in the culture vessel, whilst the desired cells and/or desired molecules present in the culture media are removed. Alternatively, the cells and/or desired molecules may be specifically retained in the culture bag, or other suitable culture vessel, by interaction with magnetic particles that have been coated with specific molecules as described herein that bind to the desired cells and/or molecules. The built-in magnetic or magnetizable device enables the washing of cell populations and replacement of media in the cell culture bag by magnetically immobilizing/concentrating cells with specific particles and flowing media and or other solutions through the bag. This device effectively eliminates the need for a separate magnetic separation device by providing a fully integrated system, thereby reducing process time and manual operations for tubing connectors, reducing the number of containers used in processing and reducing the likelihood of contamination through the number of tube and container connections required. This integrated magnetic or magnetizable device-culture system also reduces the volumes needed in the culture processing and formulation.

The combination of a force which induces the concentration of cells, ligation of cell surface moieties, and culturing cells in a rocking, closed system, results in a profound enhancement in activation and expansion of these cells (see e.g., U.S. Patent Application Publication No. 20060121005). Accordingly, in one embodiment, a bioreactor with a base rocker platform is used, for example such as "The Wave" (Wave Biotech LLC, Bedminster, N.J.), that allows for varying rates of rocking and at a variety of different rocking angles. The skilled artisan will recognize that any platform that allows for the appropriate motion for optimal expansion of the cells is within the context of the present invention. In certain embodiments, the methods of stimulation and expansion of the present invention provide for rocking the culture container during the process of culturing at 1, 2, 3, 4, 5, 6, 7, 8, 9, 10, 11, 12, 13, 14, 15, 16, 17, 18, 19, or 20 rocks per minute. In certain embodiments, the methods of stimulation and expansion of the present invention provide for the angle of the rocking platform to be set at 1.5°, 2°, 2.5°, 3°, 3.5°, 4°, 4.5°, 5°, 5.5°, 6°, 6.5°, 7°, 7.5°, 8°, 8.5°, or 9.0°.

In certain embodiments, the capacity of the bioreactor container ranges from about 0.1 liter to about 200 liters of medium. The skilled artisan will readily appreciate that the volume used for culture will vary depending on the number of starting cells and on the final number of cells desired. In particular embodiments, the cells of the present invention, such as T cells are seeded at an initial concentration of about $0.2 \times 10^6$ cells/ml to about $5 \times 10^6$ cells/ml, and any concentration therebetween. In one particular embodiment, the cells may be cultured initially in a static environment and transferred to a bioreactor on a rocking platform after 1, 2, 3, 4, 5, 6, 7, 8, or more days of culture. In a related embodiment, the entire process of stimulation, activation, and expansion takes place in a bioreactor comprising a rocking platform and an integrated magnet, as described above. Illustrative bioreactors include, but are not limited to, "The Wave".

In one particular embodiment, the cell stimulation methods of the present invention are carried out in a closed system, such as a bioreactor, that allows for perfusion of medium at varying rates, such as from about 0.1 ml/minute to about 10 ml/minute. Accordingly, in certain embodiments, the container of such a closed system comprises an outlet filter, an inlet filter, and a sampling port for sterile transfer to and from the closed system. In other embodiments, the container of such a closed system comprises a syringe pump and control for sterile transfer to and from the closed system. Further embodiments provide for a mechanism, such as a load cell, for controlling media in-put and out-put by continuous monitoring of the weight of the bioreactor container. In one embodiment the system comprises a gas manifold. In another embodiment, the bioreactor of the present invention comprises a $CO_2$ gas mix rack that supplies a mixture of ambient air and $CO_2$ to the bioreactor container and maintains the container at positive pressure. In another embodiment, the bioreactor of the present invention comprises a variable heating element.

In one embodiment, media is allowed to enter the container starting on day 2, 3, 4, 5, or 6 at about 0.5 to 5.0 liters per day until the desired final volume is achieved. In one preferred embodiment, media enters the container at 2 liters per day starting at day 4, until the volume reaches 10 liters. Once desired volume is achieved, perfusion of media can be initiated. In certain embodiments, perfusion of media through the system is initiated on about day 2, 3, 4, 5, 6, 7, 8, 9, 10, 11, or 12 of culture. In one embodiment, perfusion is initiated when the volume is at about 0.1 liter to about 200 liters of media. In one particular embodiment, perfusion is initiated when the final volume is at 4, 5, 6, 7, 8, 9, 10, or 20 liters or higher volume. The rate of perfusion can be from about 0.5 ml/minute to about 10 ml/minute. In certain embodiments, the perfusion rate is about 1, 2, 2.5, 3, 3.5, 4, 4.5, 5, 5.5, 6, 6.5, 7, 7.5, or 8.0 mls/minute.

In a further embodiment of the present invention, the cells, such as T cells, are cultured for up to 5 days in a closed, static system and then transferred to a closed system that comprises a rocking element to allow rocking of the culture container at varying speeds.

In certain aspects, the methodologies of the present invention provide for the expansion of cells, such as T cells, to a concentration of about between $6 \times 10^6$ cell/ml and about $90 \times 10^6$ cells/ml in less than about two weeks. In particular the methodologies herein provide for the expansion of T cells to a concentration of about 10, 15, 20, 25, 30, 35, 40, 45, 50, 55, 60, 65, 70, 75, 80, or $85 \times 10^6$ cells/ml and all concentrations therein. In certain embodiments, the cells reach a desired concentration, such as any of those listed above, by about day 5, 6, 7, 8, 9, 10, 11, or 12 of culture. In one embodiment, the T cells expand by at least about 1.5 fold in about 24 hours from about day 4 to about day 12 of culture. In one embodiment, the cells, such as T cells, expand from a starting number of cells of about $100 \times 10^6$ to a total of about $500 \times 10^9$ cells in less than about two weeks. In further embodiments, the T cells expand from a starting number of cells of about $500 \times 10^6$ to a total of about $500 \times 10^9$ cells in less than about two weeks. In related embodiments, the cells expand from a starting number of about $100\text{-}500 \times 10^6$ to a total of about 200, 300, or $400 \times 10^9$ cells in less than about two weeks.

Although the antibodies used in the methods described herein can be readily obtained from public sources, such as the ATCC, antibodies to T cell accessory molecules and the CD3 complex can be produced by standard techniques. Methodologies for generating antibodies for use in the methods of the invention are well-known in the art and are discussed in further detail herein.

Agent/Ligand Immobilization on a Surface

As indicated above, the methods of the present invention preferably use agents/ligands bound to a surface. The surface may be any surface capable of having an agent/ligand bound thereto or integrated into and that is biocompatible, that is, substantially non-toxic to the target cells to be stimulated. The biocompatible surface may be biodegradable or non-biodegradable. The surface may be natural or synthetic, and a synthetic surface may be a polymer. The surface may comprise collagen, purified proteins, purified peptides, polysaccharides, glycosaminoglycans, or extracellular matrix compositions. A polysaccharide may include for example, cellulose, agarose, dextran, chitosan, hyaluronic acid, or alginate. Other polymers may include polyesters, polyethers, polyanhydrides, polyalkylcyanoacryllates, polyacrylamides, polyorthoesters, polyphosphazenes, polyvinylacetates, block copolymers, polypropylene, polytetrafluorethylene (PTFE), or polyurethanes. The polymer may be lactic acid or a copolymer. A copolymer may comprise lactic acid and glycolic acid (PLGA). Non-biodegradable surfaces may include polymers, such as poly(dimethylsiloxane) and poly(ethylene-vinyl acetate). Biocompatible surfaces include for example, glass (e.g., bioglass), collagen, metal, hydroxyapatite, aluminate, bioceramic materials, hyaluronic acid polymers, alginate, acrylic ester polymers, lactic acid polymer, glycolic acid polymer, lactic acid/glycolic acid polymer, purified proteins, purified peptides, or extracellular matrix compositions. Other polymers comprising a surface may include glass, silica, silicon, hydroxyapatite, hydrogels, collagen, acrolein, polyacrylamide, polypropylene, polystyrene, nylon, or any number of plastics or synthetic organic polymers, or the like. The surface may comprise a biological structure, such as a liposome or a cell. In this regard, the surface may comprise an artificial APC such as those described in U.S. Patent Application Publication Nos. 20040101519 and 20060034810. The surface may be in the form of a lipid, a plate, bag, pellet, fiber, mesh, or particle. A particle may include, a colloidal particle, a microsphere, nanoparticle, a bead, or the like. In the various embodiments, commercially available surfaces, such as beads or other particles, are useful (e.g., Miltenyi Particles, Miltenyi Biotec, Germany; Sepharose beads, Pharmacia Fine Chemicals, Sweden; DYNABEADS™, Dynal Inc., New York; PURABEADS™, Prometic Biosciences).

When beads are used, the bead may be of any size that effectuates target cell stimulation. In one embodiment, beads are preferably from about 5 nanometers to about 500 μm in size. Accordingly, the choice of bead size depends on the particular use the bead will serve. For example, if the bead is used for monocyte depletion, a small size is chosen to facilitate monocyte ingestion (e.g., 2.8 μm and 4.5 μm in diameter or any size that may be engulfed, such as nanometer sizes); however, when separation of beads by filtration is desired, bead sizes of no less than 50 μm are typically used. Further, when using paramagnetic beads, the beads typically range in size from about 2.8 μm to about 500 μm and more preferably from about 2.8 μm to about 50 μm. Lastly, one may choose to use super-paramagnetic nanoparticles which can be as small as about $10^{-5}$ nm. Accordingly, as is readily apparent from the discussion above, virtually any particle size may be utilized.

An agent may be attached or coupled to, or integrated into a surface by a variety of methods known and available in the art. The agent may be a natural ligand, a protein ligand, or a synthetic ligand. The attachment may be covalent or noncovalent, electrostatic, or hydrophobic and may be accomplished by a variety of attachment means, including for example, chemical, mechanical, enzymatic, electrostatic, or other means whereby a ligand is capable of stimulating the cells. For example, the antibody to a ligand first may be attached to a surface, or avidin or streptavidin may be attached to the surface for binding to a biotinylated ligand. The antibody to the ligand may be attached to the surface via an antiidiotype antibody. Another example includes using protein A or protein G, or other non-specific antibody binding molecules, attached to surfaces to bind an antibody. Alternatively, the ligand may be attached to the surface by chemical means, such as cross-linking to the surface, using commercially available cross-linking reagents (Pierce, Rockford, Ill.) or other means. In certain embodiments, the ligands are covalently bound to the surface. Further, in one embodiment, commercially available tosyl-activated DYNABEADS™ or DYNABEADS™ with epoxy-surface reactive groups are incubated with the polypeptide ligand of interest according to the manufacturer's instructions. Briefly, such conditions typically involve incubation in a phosphate buffer from pH 4 to pH 9.5 at temperatures ranging from 4 to 37 degrees C.

In one aspect, the agent, such as certain ligands may be of singular origin or multiple origins and may be antibodies or fragments thereof while in another aspect, when utilizing T cells, the co-stimulatory ligand is a B7 molecule (e.g., B7-1, B7-2). These ligands are coupled to the surface by any of the different attachment means discussed above. The B7 molecule to be coupled to the surface may be isolated from a cell expressing the co-stimulatory molecule, or obtained using standard recombinant DNA technology and expression systems that allow for production and isolation of the co-stimulatory molecule(s) as described herein. Fragments, mutants, or variants of a B7 molecule that retain the capability to trigger a co-stimulatory signal in T cells when coupled to the surface of a cell can also be used. Furthermore, one of ordinary skill in the art will recognize that any ligand useful in the activation and induction of proliferation of a subset of T cells may also be immobilized on beads or culture vessel surfaces or any surface. In addition, while covalent binding of the ligand to the surface is one preferred methodology, adsorption or capture by a secondary monoclonal antibody may also be used. The amount of a particular ligand attached to a surface may be readily determined by flow cytometric analysis if the surface is that of beads or determined by enzyme-linked immunosorbent assay (ELISA) if the surface is a tissue culture dish, mesh, fibers, bags, for example.

In a particular embodiment, the stimulatory form of a B7 molecule or an anti-CD28 antibody or fragment thereof is attached to the same solid phase surface as the agent that stimulates the TCR/CD3 complex, such as an anti-CD3 antibody. In an additional embodiment, the stimulatory form of a 4-1BB molecule or an anti-4-1BB antibody or fragment thereof is attached to the same solid phase surface as the agent that stimulates the TCR/CD3 complex, such as an anti-CD3 antibody. In addition to anti-CD3 antibodies, other antibodies that bind to receptors that mimic antigen signals may be used. For example, the beads or other surfaces may be coated with combinations of anti-CD2 antibodies and a B7 molecule and in particular anti-CD3 antibodies and anti-CD28 antibodies. In further embodiments, the surfaces may be coated with three or more agents, such as combinations of any of the agents described herein, for example, anti-CD3 antibodies, anti-CD28 antibodies, and anti-4-1BB antibodies.

When coupled to a surface, the agents may be coupled to the same surface (i.e., in "cis" formation) or to separate surfaces (i.e., in "trans" formation). Alternatively, one agent may be coupled to a surface and the other agent in solution. In one embodiment, the agent providing the co-stimulatory signal is bound to a cell surface and the agent providing the primary activation signal is in solution or coupled to a surface. In a preferred embodiment, the two agents are immobilized on beads, either on the same bead, i.e., "cis," or to separate beads, i.e., "trans." By way of example, the agent providing the primary activation signal is an anti-CD3 antibody and the agent providing the co-stimulatory signal is an anti-CD28 antibody; and both agents are co-immobilized to the same bead in equivalent molecular amounts. In one embodiment, a 1:1 ratio of each antibody bound to the beads for $CD4^+$ T cell expansion and T cell growth is used. In certain aspects of the present invention, a ratio of anti CD3:CD28 antibodies bound to the beads is used such that an increase in T cell expansion is observed as compared to the expansion observed using a ratio of 1:1. In one particular embodiment an increase of from about 0.5 to about 3 fold is observed as compared to the expansion observed using a ratio of 1:1. In one embodiment, the ratio of CD3:CD28 antibody bound to the beads ranges from 100:1 to 1:100 and all integer values there between. In one aspect of the present invention, more anti-CD28 antibody is bound to the particles than anti-CD3 antibody, i.e. the ratio of CD3:CD28 is less than one. In certain embodiments of the invention, the ratio of anti CD28 antibody to anti CD3 antibody bound to the beads is greater than 2:1. In one particular embodiment, a 1:100 CD3:CD28 ratio of antibody bound to beads is used. In another embodiment, a 1:75 CD3:CD28 ratio of antibody bound to beads is used. In a further embodiment, a 1:50 CD3:CD28 ratio of antibody bound to beads is used. In another embodiment, a 1:30 CD3:CD28 ratio of antibody bound to beads is used. In one preferred embodiment, a 1:10 CD3:CD28 ratio of antibody bound to beads is used. In another embodiment, a 1:3 CD3:CD28 ratio of antibody bound to the beads is used. In yet another embodiment, a 3:1 CD3:CD28 ratio of antibody bound to the beads is used.

In certain aspects of the present invention, three or more agents are coupled to a surface. In certain embodiments, the agents may be coupled to the same surface (i.e., in "cis" formation) or to separate surfaces (i.e., in "trans" formation). Alternatively, one or more agents may be coupled to a surface and the other agent or agents may be in solution.
Agents Agents contemplated by the present invention include protein ligands, natural ligands, and synthetic ligands. Agents that can bind to cell surface moieties, and under certain conditions, cause ligation and aggregation that leads to signaling include, but are not limited to, lectins (for example, PHA, lentil lectins, concanavalin A), antibodies, antibody fragments, peptides, polypeptides, glycopeptides, receptors, B cell receptor and T cell receptor ligands, extracellular matrix components, steroids, hormones (for example, growth hormone, corticosteroids, prostaglandins, tetra-iodo thyronine), bacterial moieties (such as lipopolysaccharides), mitogens, antigens (e.g., JCV proteins or antigens derived therefrom; see e.g., U.S. Pat. No. 6,238,859), superantigens and their derivatives, growth factors, cytokine, viral proteins (for example, HIV gp-120), adhesion molecules (such as, L-selectin, LFA-3, CD54, LFA-1), chemokines, and small molecules. The agents may be isolated from natural sources such as cells, blood products, and tissues, or isolated from cells propagated in vitro, or prepared recombinantly, or by other methods known to those with skill in the art.

In one aspect of the present invention, when it is desirous to stimulate T cells, useful agents include ligands that are capable of binding the CD3/TCR complex, CD2, and/or CD28 and initiating activation or proliferation, respectively. Accordingly, the term ligand includes those proteins that are the "natural" ligand for the cell surface protein, such as a B7 molecule for CD28, as well as artificial ligands such as antibodies directed to the cell surface protein. Such antibodies and fragments thereof may be produced in accordance with conventional techniques, such as hybridoma methods and recombinant DNA and protein expression techniques. Useful antibodies and fragments may be derived from any species, including humans, or may be formed as chimeric proteins, which employ sequences from more than one species.

Methods well known in the art may be used to generate antibodies, polyclonal antisera, or monoclonal antibodies that are specific for a ligand. Antibodies also may be produced as genetically engineered immunoglobulins (Ig) or Ig fragments designed to have desirable properties. For example, by way of illustration and not limitation, antibodies may include a recombinant IgG that is a chimeric fusion protein having at least one variable (V) region domain from a first mammalian species and at least one constant region domain from a second distinct mammalian species. Most commonly, a chimeric antibody has murine variable region sequences and human constant region sequences. Such a murine/human chimeric immunoglobulin may be "humanized" by grafting the complementarity determining regions (CDRs), which confer binding specificity for an antigen, derived from a murine antibody into human-derived V region framework regions and human-derived constant regions. Fragments of these molecules may be generated by proteolytic digestion, or optionally, by proteolytic digestion followed by mild reduction of disulfide bonds and alkylation, or by recombinant genetic engineering techniques.

Antibodies are defined to be "immunospecific" if they specifically bind the ligand with an affinity constant, $K_a$, of greater than or equal to about $10^4$ $M^{-1}$, preferably of greater than or equal to about $10^5$ $M^{-1}$, more preferably of greater than or equal to about $10^6$ $M^{-1}$, and still more preferably of greater than or equal to about $10^7$ $M^{-1}$. Affinities of binding partners or antibodies can be readily determined using conventional techniques, for example, those described by Scatchard et al. (*Ann. N.Y. Acad. Sci. USA* 51:660, 1949) or by surface plasmon resonance (BIAcore, Biosensor, Piscataway, N.J.) See, e.g., Wolff et al., *Cancer Res.*, 53:2560-2565, 1993).

Antibodies may generally be prepared by any of a variety of techniques known to those having ordinary skill in the art (See, e.g., Harlow et al., *Antibodies: A Laboratory Manual*, 1988, Cold Spring Harbor Laboratory). In one such technique, an animal is immunized with the ligand as antigen to generate polyclonal antisera. Suitable animals include rabbits, sheep, goats, pigs, cattle, and may include smaller mammalian species, such as, mice, rats, and hamsters.

An immunogen may be comprised of cells expressing the ligand, purified or partially purified ligand polypeptides or variants or fragments thereof, or ligand peptides. Ligand peptides may be generated by proteolytic cleavage or may be chemically synthesized. Peptides for immunization may be selected by analyzing the primary, secondary, or tertiary structure of the ligand according to methods know to those skilled in the art in order to determine amino acid sequences more likely to generate an antigenic response in a host animal (See, e.g., Novotny, *Mol. Immunol.* 28:201-207, 1991; Berzoksky, *Science* 229:932-40, 1985).

Preparation of the immunogen may include covalent coupling of the ligand polypeptide or variant or fragment thereof, or peptide to another immunogenic protein, such as, keyhole limpet hemocyanin or bovine serum albumin. In addition, the peptide, polypeptide, or cells may be emulsified in an adjuvant (See Harlow et al., *Antibodies: A Laboratory Manual*, 1988 Cold Spring Harbor Laboratory). In general, after the first injection, animals receive one or more booster immunizations according to a preferable schedule for the animal species. The immune response may be monitored by periodically bleeding the animal, separating the sera, and analyzing the sera in an immunoassay, such as an Ouchterlony assay, to assess the specific antibody titer. Once an antibody titer is established, the animals may be bled periodically to accumulate the polyclonal antisera. Polyclonal antibodies that bind specifically to the ligand polypeptide or peptide may then be purified from such antisera, for example, by affinity chromatography using protein A or using the ligand polypeptide or peptide coupled to a suitable solid support.

Monoclonal antibodies that specifically bind ligand polypeptides or fragments or variants thereof may be prepared, for example, using the technique of Kohler and Milstein (*Nature*, 256:495-497, 1975; *Eur. J. Immunol.* 6:511-519, 1976) and improvements thereto. Hybridomas, which are immortal eukaryotic cell lines, may be generated that produce antibodies having the desired specificity to a the ligand polypeptide or variant or fragment thereof. An animal—for example, a rat, hamster, or preferably mouse—is immunized with the ligand immunogen prepared as described above. Lymphoid cells, most commonly, spleen cells, obtained from an immunized animal may be immortalized by fusion with a drug-sensitized myeloma cell fusion partner, preferably one that is syngeneic with the immunized animal. The spleen cells and myeloma cells may be combined for a few minutes with a membrane fusion-promoting agent, such as polyethylene glycol or a nonionic detergent, and then plated at low density on a selective medium that supports the growth of hybridoma cells, but not myeloma cells. A preferred selection media is HAT (hypoxanthine, aminopterin, thymidine). After a sufficient time, usually about 1 to 2 weeks, colonies of cells are observed. Single colonies are isolated, and antibodies produced by the cells may be tested for binding activity to the ligand polypeptide or variant or fragment thereof. Hybridomas producing antibody with high affinity and specificity for the ligand antigen are preferred. Hybridomas that produce monoclonal antibodies that specifically bind to a ligand polypeptide or variant or fragment thereof are contemplated by the present invention.

Monoclonal antibodies may be isolated from the supernatants of hybridoma cultures. An alternative method for production of a murine monoclonal antibody is to inject the hybridoma cells into the peritoneal cavity of a syngeneic mouse. The mouse produces ascites fluid containing the monoclonal antibody. Contaminants may be removed from the antibody by conventional techniques, such as chromatography, gel filtration, precipitation, or extraction.

Human monoclonal antibodies may be generated by any number of techniques. Methods include but are not limited to, Epstein Barr Virus (EBV) transformation of human peripheral blood cells (see, U.S. Pat. No. 4,464,456), in vitro immunization of human B cells (see, e.g., Boerner et al., *J. Immunol.* 147:86-95, 1991), fusion of spleen cells from immunized transgenic mice carrying human immunoglobulin genes and fusion of spleen cells from immunized transgenic mice carrying immunoglobulin genes inserted by yeast artificial chromosome (YAC) (see, e.g., U.S. Pat. No. 5,877,397; Bruggemann et al., *Curr. Opin. Biotechnol.* 8:455-58, 1997; Jakobovits et al., *Ann. N.Y. Acad. Sci.* 764:525-35, 1995), or isolation from human immunoglobulin V region phage libraries.

Chimeric antibodies and humanized antibodies for use in the present invention may be generated. A chimeric antibody has at least one constant region domain derived from a first mammalian species and at least one variable region domain derived from a second distinct mammalian species (See, e.g., Morrison et al., *Proc. Natl. Acad. Sci. USA*, 81:6851-55, 1984). Most commonly, a chimeric antibody may be constructed by cloning the polynucleotide sequences that encode at least one variable region domain derived from a non-human monoclonal antibody, such as the variable region derived from a murine, rat, or hamster monoclonal antibody, into a vector containing sequences that encode at least one human constant region. (See, e.g., Shin et al., *Methods Enzymol.* 178:459-76, 1989; Walls et al., *Nucleic Acids Res.* 21:2921-29, 1993). The human constant region chosen may depend upon the effector functions desired for the particular antibody. Another method known in the art for generating chimeric antibodies is homologous recombination (U.S. Pat. No. 5,482,856). Preferably, the vectors will be transfected into eukaryotic cells for stable expression of the chimeric antibody.

A non-human/human chimeric antibody may be further genetically engineered to create a "humanized" antibody. Such an antibody has a plurality of CDRs derived from an immunoglobulin of a non-human mammalian species, at least one human variable framework region, and at least one human immunoglobulin constant region. Humanization may yield an antibody that has decreased binding affinity when compared with the non-human monoclonal antibody or the chimeric antibody. Those having skill in the art, therefore, use one or more strategies to design humanized antibodies.

Within certain embodiments, the use of antigen-binding fragments of antibodies may be preferred. Such fragments include Fab fragments or F(ab')$_2$ fragments, which may be prepared by proteolytic digestion with papain or pepsin, respectively. The antigen binding fragments may be separated from the Fc fragments by affinity chromatography, for example, using immobilized protein A or immobilized ligand polypeptide or a variant or a fragment thereof. An alternative method to generate Fab fragments includes mild reduction of F(ab')$_2$ fragments followed by alkylation (See, e.g., Weir, *Handbook of Experimental Immunology*, 1986, Blackwell Scientific, Boston).

Non-human, human, or humanized heavy chain and light chain variable regions of any of the above described Ig molecules may be constructed as single chain Fv (sFv) fragments (single chain antibodies). See, e.g., Bird et al., *Science* 242: 423-426, 1988; Huston et al., *Proc. Natl. Acad. Sci. USA* 85:5879-5883, 1988. Multi-functional fusion proteins may be generated by linking polynucleotide sequences encoding an sFv in-frame with polynucleotide sequences encoding various effector proteins. These methods are known in the art, and are disclosed, for example, in EP-B1-0318554, U.S. Pat. Nos. 5,132,405, 5,091,513, and 5,476,786.

An additional method for selecting antibodies that specifically bind to a ligand polypeptide or variant or fragment thereof is by phage display (See, e.g., Winter et al., *Annul. Rev. Immunol.* 12:433-55, 1994; Burton et al., *Adv. Immunol.* 57:191-280, 1994). Human or murine immunoglobulin variable region gene combinatorial libraries may be created in phage vectors that can be screened to select Ig fragments (Fab, Fv, sFv, or multimers thereof) that bind specifically to a ligand polypeptide or variant or fragment thereof (See, e.g., U.S. Pat. No. 5,223,409; Huse et al., *Science* 246:1275-81, 1989; Kang et al., *Proc. Natl. Acad. Sci. USA* 88:4363-66, 1991; Hoogenboom et al., *J. Molec. Biol.* 227:381-388, 1992; Schlebusch et al., *Hybridoma* 16:47-52, 1997 and references cited therein).

Methods of Use and Pharmaceutical Compositions

Generally, the cells activated and expanded as described herein may be utilized in the treatment and prevention of diseases that arise in individuals who are immunocompromised. In particular, the autologous activated and expanded T cells of the invention are used in the treatment of PML. In certain embodiments, the cells of the invention are used in the treatment of patients at risk for developing PML, such as MS patients taking natalizumab, psoriasis patients taking efalizumab, HIV infected individuals, or other immunocompromised invidivuals with a risk of developing PML. Thus, the present invention provides methods for the treatment or prevention of PML comprising administering to a subject in need thereof, a therapeutically effective amount of the T cells activated and expanded using the methods described herein.

The T cell populations of the present invention may be administered either alone, or as a pharmaceutical composition in combination with diluents and/or with other components such as IL-2 or other cytokines or cell populations. Briefly, pharmaceutical compositions of the present invention may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

The immune response induced in a subject by administering T cells activated and expanded using the methods described herein, or other methods known in the art wherein T cells are stimulated and expanded to therapeutic levels, may include cellular immune responses mediated by cytotoxic T cells, capable of killing tumor and infected cells, regulatory T cells, and helper T cell responses. Humoral immune responses, mediated primarily by helper T cells capable of activating B cells thus leading to antibody production, may also be induced. A variety of techniques may be used for analyzing the type of immune responses induced by the compositions of the present invention, which are well described in the art; e.g., Coligan et al. Current Protocols in Immunology, John Wiley & Sons Inc. (1994).

When "an immunologically effective amount", "an anti-tumor effective amount", "an tumor-inhibiting effective amount", or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^9$ cells/kg body weight, preferably $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

Typically, in adoptive immunotherapy studies, antigen-specific T cells are administered approximately at $2\times10^9$ to $2\times10^{11}$ cells to the patient. (See, e.g., U.S. Pat. No. 5,057,423). In some aspects of the present invention, particularly in the use of allogeneic or xenogeneic cells, lower numbers of cells, in the range of $10^6$/kilogram ($10^6$-$10^{11}$ per patient) may be administered. In certain embodiments, T cells are administered at $1\times10^5$, $1\times10^6$, $1\times10^7$, $1\times10^8$, $2\times10^8$, $2\times10^9$, $1\times10^{10}$, $2\times10^{10}$, $1\times10^{11}$, $5\times10^{11}$, or $1\times10^{12}$ cells to the subject. T cell compositions may be administered multiple times at dosages within these ranges. The cells may be autologous or heterologous to the patient undergoing therapy. If desired, the treatment may also include administration of mitogens (e.g., PHA) or lymphokines, cytokines, and/or chemokines (e.g., GM-CSF, IL-4, IL-7, IL-13, Flt3-L, RANTES, MIP1α, etc.) as described herein to enhance induction of the immune response.

In certain embodiments, it may be desired to administer activated T cells to a subject and then subsequently redraw blood (or have a leukapheresis performed), activate T cells therefrom according to the present invention, and reinfuse the patient with these activated and expanded T cells. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, or 100 cc. Not to be bound by theory, using this multiple blood draw/multiple reinfusion protocol, may select out certain populations of T cells.

The administration of the subject compositions may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous (i.v.) injection, or intraperitoneally. In one embodiment, the T cell compositions of the present invention are administered to a patient by intradermal or subcutaneous injection. In another embodiment, the T cell compositions of the present invention are preferably administered by i.v. injection. The compositions of T cells may be injected directly into a tumor, lymph node, or site of infection.

In yet another embodiment, the pharmaceutical composition can be delivered in a controlled release system. In one embodiment, a pump may be used (see Langer, 1990, Science 249:1527-1533; Sefton 1987, CRC Crit. Ref. Biomed. Eng. 14:201; Buchwald et al., 1980; Surgery 88:507; Saudek et al., 1989, N. Engl. J. Med. 321:574). In another embodiment, polymeric materials can be used (see Medical Applications of Controlled Release, 1974, Langer and Wise (eds.), CRC Pres., Boca Raton, Fla.; Controlled Drug Bioavailability, Drug Product Design and Performance, 1984, Smolen and Ball (eds.), Wiley, New York; Ranger and Peppas, 1983; J. Macromol. Sci. Rev. Macromol. Chem. 23:61; see also Levy et al., 1985, Science 228:190; During et al., 1989, Ann. Neurol. 25:351; Howard et al., 1989, J. Neurosurg. 71:105). In yet another embodiment, a controlled release system can be placed in proximity of the therapeutic target, thus requiring only a fraction of the systemic dose (see, e.g., Medical Applications of Controlled Release, 1984, Langer and Wise (eds.), CRC Pres., Boca Raton, Fla., vol. 2, pp. 115-138).

The T cell compositions of the present invention may also be administered using any number of matrices. Matrices have been utilized for a number of years within the context of tissue engineering (see, e.g., Principles of Tissue Engineering (Lanza, Langer, and Chick (eds.)), 1997. The present invention utilizes such matrices within the novel context of acting as an artificial lymphoid organ to support, maintain, or modulate the immune system, typically through modulation of T cells. Accordingly, the present invention can utilize those matrix compositions and formulations which have demonstrated utility in tissue engineering. Accordingly, the type of matrix that may be used in the compositions, devices and methods of the invention is virtually limitless and may include both biological and synthetic matrices. In one particular example, the compositions and devices set forth by U.S. Pat. Nos. 5,980,889; 5,913,998; 5,902,745; 5,843,069; 5,787,900; or 5,626,561 are utilized. Matrices comprise features commonly associated with being biocompatible when administered to a mammalian host. Matrices may be formed from both natural or synthetic materials. The matrices may be non-biodegradable in instances where it is desirable to leave permanent structures or removable structures in the body of an animal, such as an implant; or biodegradable. The matrices may take the form of sponges, implants, tubes, telfa pads, fibers, hollow fibers, lyophilized components, gels, powders, porous compositions, or nanoparticles. In addition, matrices can be designed to allow for sustained release seeded cells or produced cytokine or other active agent. In certain embodiments, the matrix of the present invention is flexible and elastic, and may be described as a semisolid scaffold that is permeable to substances such as inorganic salts, aqueous fluids and dissolved gaseous agents including oxygen.

A matrix is used herein as an example of a biocompatible substance. However, the current invention is not limited to matrices and thus, wherever the term matrix or matrices appears these terms should be read to include devices and other substances which allow for cellular retention or cellular traversal, are biocompatible, and are capable of allowing traversal of macromolecules either directly through the substance such that the substance itself is a semi-permeable membrane or used in conjunction with a particular semi-permeable substance.

In certain embodiments of the present invention, cells activated and expanded using the methods described herein, or other methods known in the art where T cells are expanded to therapeutic levels, are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or efalizumab treatment for psoriasis patients or other treatments for PML patients. In further embodiments, the T cells of the invention may be used in combination with chemotherapy, radiation, irrimunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun. 73:316-321, 1991; Bierer et al., Curr. Opin. Immun 5:763-773, 1993; Isoniemi (supra)). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

The dosage of the above treatments to be administered to a patient will vary with the precise nature of the condition being treated and the recipient of the treatment. The scaling of dosages for human administration can be performed according to art-accepted practices. The dose for CAMPATH, for example, will generally be in the range 1 to about 100 mg for an adult patient, usually administered daily for a period between 1 and 30 days. The preferred daily dose is 1 to 10 mg per day although in some instances larger doses of up to 40 mg per day may be used (described in U.S. Pat. No. 6,120,766).

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1

Treatment and Resolution of PML With Autologous Lymphocyte Infusion

A 61-year old male patient was diagnosed with CLL in 1996. Prior therapy included fludarabine, rituximab and cyclophosphamide. The patient relapsed in 2007. In August 2007, the patient presented with brain lesions and hemiparesis diagnostic of PML. Progression was observed by MRI in October 2007.

An initial 130 ml sample of blood from the patient was received on Dec. 17, 2007 for preclinical evaluation of compassionate use T cell infusion. FIG. 1 shows CD45+/CD3+ T cells 10 days post stimulation with anti-CD3/anti-CD28 beads. A compassionate use IND was filed December 2007. Apheresis and T cell manufacturing with anti-CD3/CD28 beads was carried out in a GMP facility according to established methods, such as those described in U.S. Patent Application Publication No. US20060121005. $1 \times 10^{10}$ autologous CD3/CD28 activated T cells were infused into the patient on Feb. 1, 2008.

Results: CD4/CD8 T cell ratio increased from 0.5 to >1.0 after infusion. Absolute CD4 T cell count increased from 200 to 1600 cells/ml. A commensurate increase in absolute lymphocyte count was observed. *Candida* delayed type hypersensitivity reaction (DTH), originally negative, became marginally positive (3 mm)

Clinical parameters: MRI: stable to improved the 10 months post infusion. A partial resolution of hemiparesis was observed as well as normalization of performance status.

Figure 2:
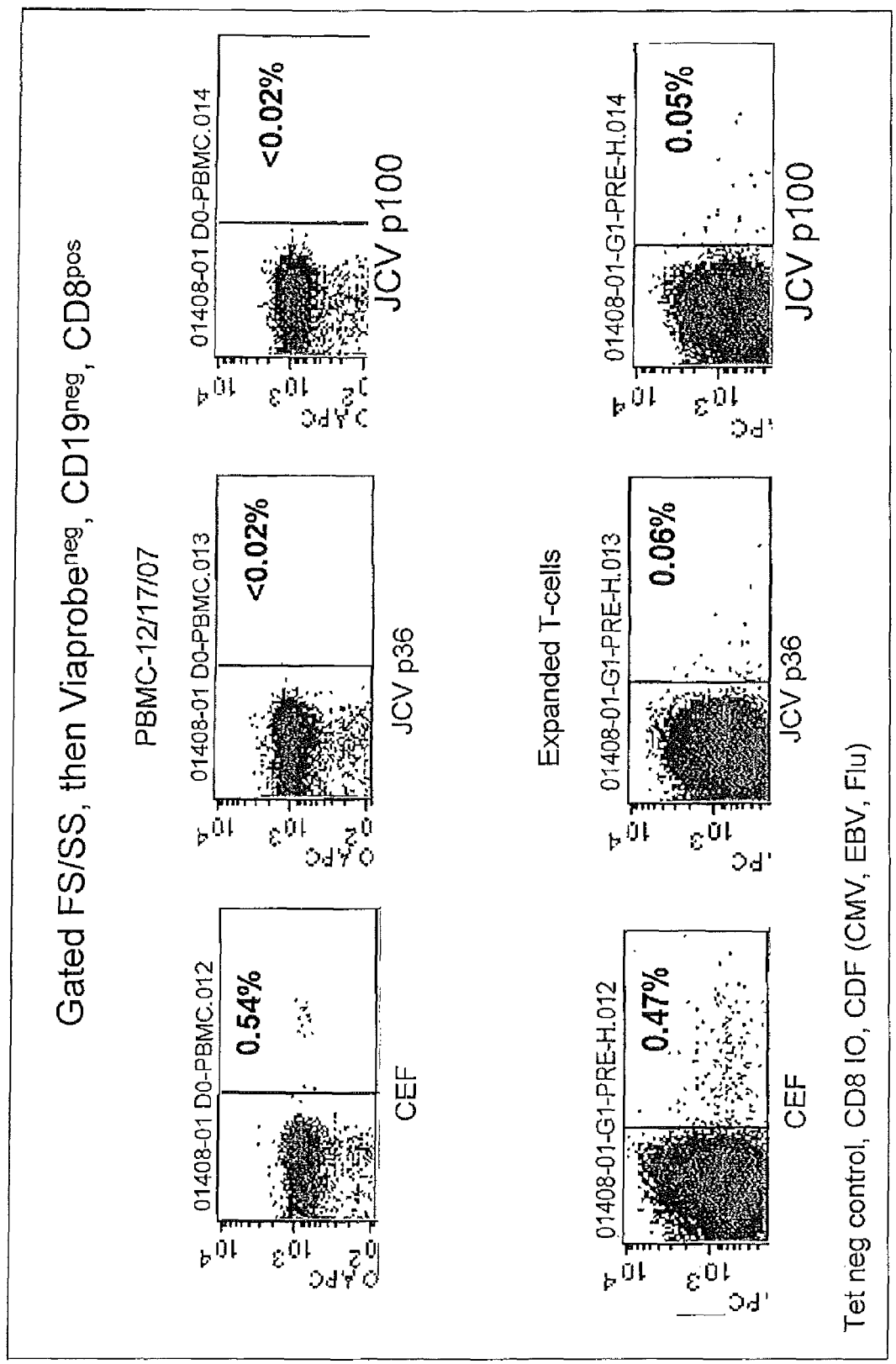
FIG. 2 shows flow cytometric analysis of virus-specific CD8 + T cells from a CLL patient with PML pre and post anti-CD3/anti-CD28 stimulation. CEF: CMV, EBV, Flu.
Figure 3:
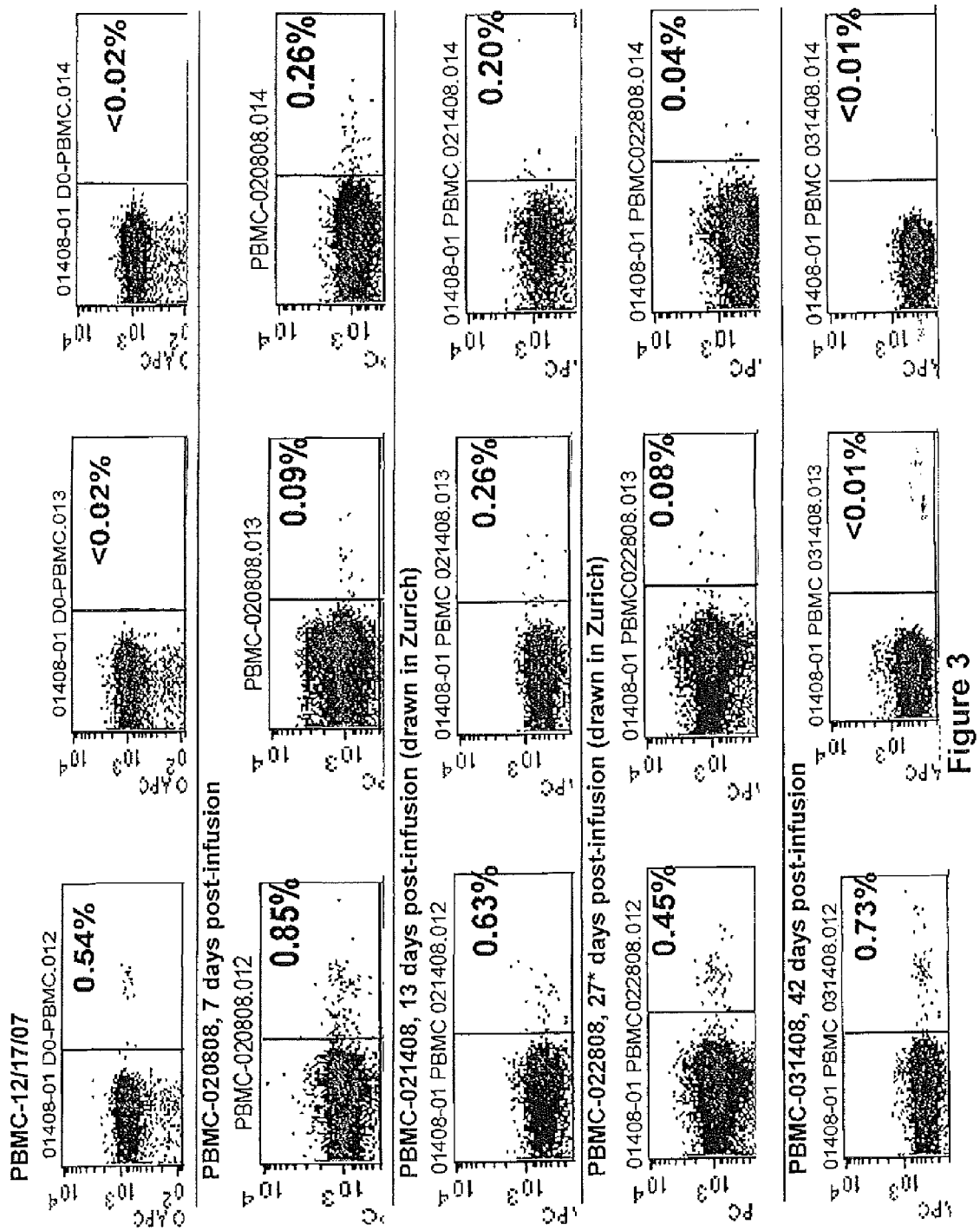
FIG. 3 shows flow cytometric analysis of virus-specific CD8 + T cells from a CLL patient with PML post anti-CD3/anti-CD28 stimulation and infusion. CEF: CMV, EBV, Flu.

Flow cytometric analysis of the patient T cells pre and post expansion and post infusion is shown in FIGS. 1-3.

Further analysis of JC virus-specific T cells post-infusion indicated a frequency of IFN-$\gamma^+$, CD69$^+$, CD4$^+$ and CD8$^+$ T cell following JC-LT stimulation of 3.65% and 0.17%, respectively. Following JC-VP1 stimulation, the respective frequencies of IFN-$\gamma^+$, CD69$^+$, CD4$^+$ and CD8$^+$ T cells were 4.06% and 0.25%. The frequency of IL-2$^+$, CD4$^+$ and CD8$^+$ T cell following JC-LT stimulation was 3.87% and 1.08%, respectively. Following JC-VP1 stimulation, the respective frequencies of IL2$^+$, CD4$^+$ and CD8$^+$ T cells were 3.34% and 0.24%. These are relatively high frequencies of virus-specific T cells, indicating a healthy JCV-specific immune reconstitution.

Thus, infusion of activated and expanded autologous T cells resulted in resolution of PML in this patient, suggesting that ALI may be an appropriate therapy for this untreatable disease.

Example 2

CD3/CD28 Beads as Artificial Antigen Presenting Cells (aAPCs) For T Cell Expansion Progressive multifocal leukoencephalopathy (PML) is a demyelinating disease caused by the polyomavirus JC (JCV), which occurs in immunosuppressed patients (Koralnik, 2006, Ann. Neurol. 60:162-73). It is a rare disease which results in inflammation of the white matter of the brain in multiple locations and carries with it a poor prognosis. It has been demonstrated that JCV-specific CD8+ CTLs (specific for two A*0201-restricted JCV epitopes, VP1(p36) and VP1(p100)) are associated with a more favorable outcome in patients with PML (Lima et al., 2007, J. Virol. 81:3361-8) and therefore immunotherapeutic approaches aimed at increasing the cellular immune response against JCV may be helpful. Without wishing to be bound by any particular theory, it is believed that CLL patients who are also diagnosed with PML, immune augmentation will be beneficial to control a JC or JC-like virus infection and provides additional rationale for the administration of polyclonal activated T-cells.

T-cell costimulation is critical for induction of full T-cell effector function, and thus represents an attractive immunotherapeutic approach for the treatment of cancer. The T-cell culture and expansion technology used in this example includes ex vivo activation of apheresed T-cells is induced by antibodies to the T-cell receptor complex accessory molecule CD3 and to the costimulatory receptor CD28, which are both immobilized on magnetic beads, and provide sufficient signals to drive the logarithmic growth of T-cells. This system, akin to "artificial antigen presenting cells," has proven to be an ideal strategy for rapid and efficient generation of large numbers of activated T-cells and supports the most efficient reported growth of human polyclonal naïve and memory CD4+ cells (Levine et al., 1997, J. Immunol. 159:5921-30). In terms of cell function, the expanded cells retain a highly diverse TCR repertoire, and, by variation of culture conditions, they can be induced to secrete cytokines characteristic of T helper 1 (Th1) or T helper 2 (Th2) cells. One important advantage of this bead-based system is that it does not cross-react with CTLA-4, thereby facilitating unopposed CD28 stimulation for more efficient expansion of T-cells. Ex vivo expansion may also indirectly enhance T-cell activity by removing T-cells from a tumor-induced immunosuppressive milieu (Bonyhadi et al., 2005, J. Immunol. 174:2366-75; Patten et al., 2005, J. Immunol. 174:6562-3; Renner et al., 1996, Blood 88:236-41; Woo et al., 2001, Cancer Res. 61:4766-72).

Bonyhadi et al (2005, J. Immunol. 174:2366-75) developed a method using anti-CD3/anti-CD28 conjugated beads that preferentially expanded T cells and eliminated leukemic cells from the CLL patient pool. In the culture, mean T cell composition increased from ~6% to >90% and leukemic B cells decreased from a mean of ~85% to 0.1% or less. Both activated CD4+ and CD8+ T cell subsets expressed an array of key effector molecules that have been shown to contribute to potent immune responses, including CD54, CD134, CD137, and CD154. The T cells were also able to secrete large amounts of type 1 cytokines such as IFN-$\gamma$ and TNF-$\alpha$ suggesting that the CD3/CD28 bead activation process favors the generation of Th1 and T cytotoxic (Tc)1 T cells, cell types that are responsible for cell mediated immune responses that are thought to play a major role in antitumor immunity. GM-CSF, which plays an important role in recruiting and promoting the differentiation of APCs, was also produced at high levels during the entire activation and expansion process. Furthermore, after expansion, there was an increase in the number of tumor-reactive T cells, the skewing in the TCR repertoire returned to normal, and the activated T cells had potent in vitro antileukemic effects. Taken together, this data suggests that the CD3/CD28 bead expanded T cells may help enhance immune responses in vivo.

Based on the above preclinical data, a Phase I/II clinical trial in patients with advanced CLL was initiated. Patients underwent leukopheresis to collect PBMCs for T cell expansion using the Xcyte™ anti-CD3/anti-CD28 Dynabeads. Four patients were treated with a single infusion of the "Xcellerated" T cells, three at the $1 \times 10^{10}$ dose and one at the $3 \times 10^{10}$ dose. The T cells were well-tolerated with no Grade 3 or 4 infusional toxicities. The lymphocyte counts on the day of infusion were 210, 47, 52 and $16 \times 10^3/\text{mm}^3$, and maximal decreases in CD5+ CD19+ leukemic cells following infusion were 18%, 31%, 26% or 24% respectively, occurring on days 3, 7, 1 or 1 post-infusion respectively. Absolute T cell counts prior to treatment were 5.9, 1.8, 2.5, or $1.9 \times 10^3/\text{mm}^3$ and increased in each patient following Xcellerated T Cell infusion, with maximal increases in each subject of 23%, 96%, 44%, or 82% respectively, occurring at days 21, 14, 14, or 7 post-infusion respectively Preliminary data from this trial suggests that a T cell dose of up to $3 \times 10^{10}$ cells could reproducibly be expanded from an apheresis unit and safely administered to CLL patients using a standard operating procedure (SOP) that removes the unwanted leukemic B cells at the start of the culture.

The safety and tolerability of ex vivo activated T-cells have been evaluated most extensively in CVPF clinical trials of hematologic malignancies such as leukemia, lymphoma, and myeloma (Laport et al., 2003, Blood 102:2004-13; Rapoport et al., 2004, Bone Marrow Transplant. 33:53-60; Rapoport et al., 2005, Nat. Med. 11:1230-7). In addition, the combination of activated autologous T-cells with chemotherapy (most notably alkylating agents) and stem cell transplantation (single and tandem) has been associated with complete and partial responses. Although these data are promising, efficacy that can be attributed specifically to the reinfusion of activated T-cells must be addressed in larger randomized clinical trials. Collectively, experience to date from protocols in which activated autologous T cell infusions were preceded by immune suppression conditioning suggests functional lymphocyte recovery can be achieved in these patients.

In a Phase I study of patients with relapsed or chemotherapy refractory Non Hodgkin's lymphoma, seventeen patients were treated with CD34+-selected hematopoietic stem cell transplant followed by infusion of autologous peripheral blood T cells stimulated ex vivo with anti-CD3 and anti-CD28 beads (Laport et al., 2003, Blood 102:2004-13). Infusions of the autologous expanded T cells were well tolerated and resulted in a rapid reconstitution of lymphocyte counts. Importantly, the expanded cells were functionally superior to those obtained directly from the patients, as determined by interferon-gamma induction. Maximal clinical responses included 5 patients with a complete response, 7 patients with a partial response and 5 patients with stable disease. At a median follow-up of 474 days (range=105-1097), 5 patients were alive with stable or relapsed disease and 3 patients remained in complete response. Thus, this Phase I trial demonstrated that adoptive transfer of expanded T-cells (1) is feasible, even in heavily pretreated patients with advanced non-Hodgkin's lymphoma, (2) may accelerate recovery of the CD4 T-cell count, and (3) has minimal to moderate infusion toxicity.

In a current phase I study of patients with purine analog-naive relapsed/refractory follicular lymphoma, patients are receiving 4 cycles of fludarabine (25 mg/m$^2$) days 1-3 and cyclophosphamide (250 mg/m$^2$) days 1-3. Four weeks after the last cycle of chemotherapy, responding patients (CR, CRu, PR) receive escalating doses of adoptive lymphocyte transfer prepared ex vivo from autologous T-cells collected prior to chemotherapy and depleted of CD4$^+$ CD25$^+$ regulatory T cells, then activated and expanded using anti-CD3 and anti-CD28. Thirteen patients have been enrolled to date. For the 9 assessable patients completing chemotherapy and T cell infusion, 7 patients achieved a complete response and 2 pts achieved a partial response. There have been no adverse events related to T-cell infusions, up to a cell dose of 10×10$^9$. Median follow-up after T cell infusion is 20 months (range: 2-42 months). CD4 counts increased in all patients by 1 month after T-cell infusion, with a median increase of 3.8 fold (n=8; range: 1.5-71). For patients at dose level 1, the median increase was 2.2 fold (n=4; range: 1.5-21); at dose level 2, it was 4.2 fold (n=4; range: 3.8-71). CD8 counts also increased, with a median increase of 8.1 fold (range: 1.0-30). All 9 patients receiving ACTC were anergic to *candida* antigen by delayed type hypersensitivity (DTH) skin testing before chemotherapy; 5 patients developed a positive DTH response to *candida* antigen 60 days after T cell infusion. From the start of therapy for patients receiving T-cells, median follow-up is 24 months (range: 6-47) with median progression-free survival of 18 months, which is significantly longer than the time to progression from last therapy (median 11 months) (p=0.01, log-rank test, FIG. 4). More rapid CD4+ and CD8+ lymphocyte recovery is observed in these patients after cyclophosphamide-fludarabine chemotherapy compared to historical controls, in addition to reconstitution of recall immunity, and a relative reduction of peripheral blood FoxP3+ regulatory T cells.

Two other trials in myeloma have been conducted in which patients receive vaccine primed activated T cells after suppression of myeloma by high-dose chemotherapy and autologous stem cell rescue (Rapoport et al., 2005, Nat. Med. 11:1230-7). In the first trial, it was observed that adoptive transfer of in-vivo vaccine-primed and ex-vivo expanded autologous T cells at about day 14 post-transplant increased CD4+ and CD8+ T cell counts at Day +42 post-transplant and induced pneumococcal conjugate vaccine-directed T and B-cell responses. Protective antibody levels were also established by Day+30, and improved proliferative capacity of cells to vaccine carrier antigen and to Staphylococcal enterotoxin B was observed. This was the first randomized adoptive immunotherapy trial to achieve successful endpoints by demonstrating that the response to vaccination could be enhanced in the presence of chemotherapy-induced lymphopenia. In a follow-up Phase I/II trial in which twenty one patients to date have received activated autologous T cells primed against the multipeptide vaccine against telomerase, survivin, and CMV, we have seen no delays in hematopoietic recovery after Day +2 transfers of the expanded T cells. In fact, T cell recovery, as measured by quantifying CD3+, CD4+, and CD8+ cells is accelerated compared to randomized and historical controls indicating possible schedule dependency of T cell infusion. The robust T cell counts can be achieved as early as Day +14 post stem cell transplant, with a median CD4 count was 1951/mcl (range 651-7668) and the median CD8 count was 4117/mcl (range 1499-39,354). The T cell recovery shows sustained levels above normal suggesting that early recovery may not be subject to normal homeostatic mechanisms.

Figure 4:
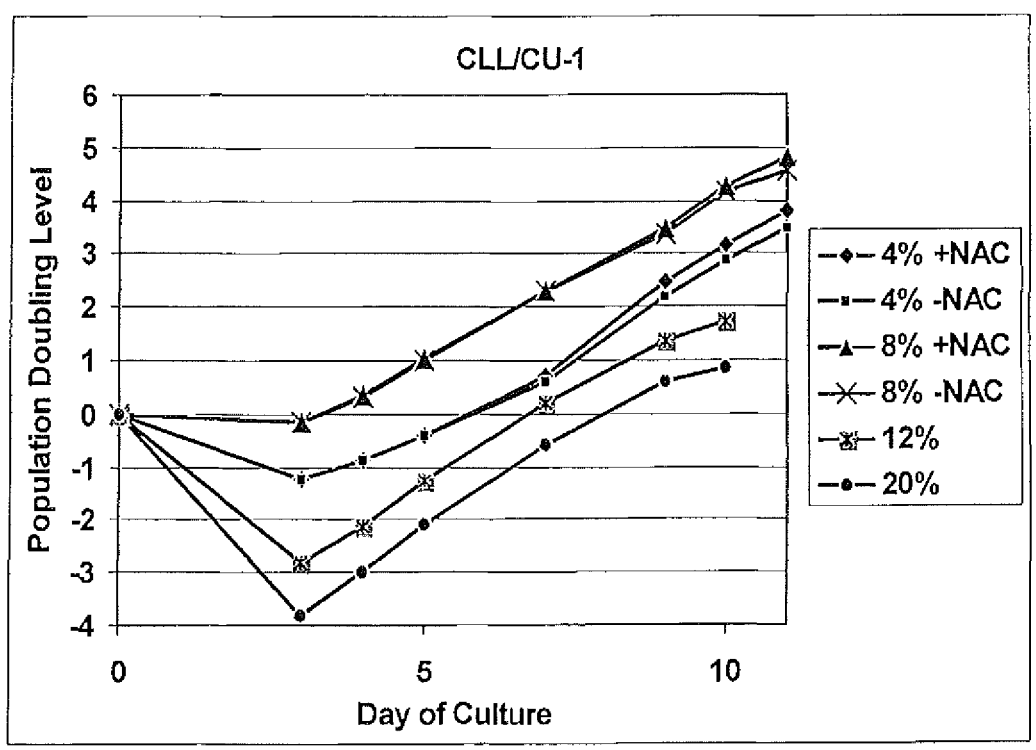
FIG. 4 is a chart demonstrating that T cells selected and expanded with anti-CD3/CD28 beads were able to be expanded under small scale conditions at least 4.3 population doublings (20-fold) under optimal conditions.
Figure 5:
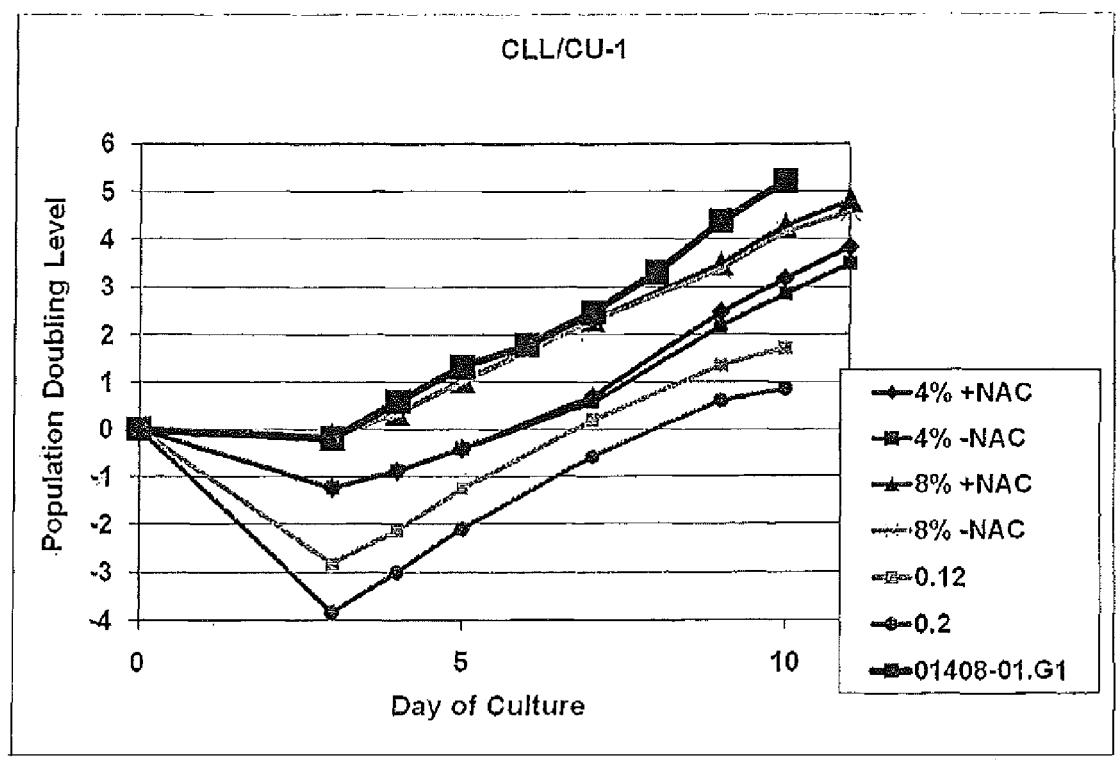
FIG. 5 is a chart demonstrating that T cells selected and expanded with anti-CD3/CD28 beads using the optimal small scale conditions in a clinical scale bioreactor can expand at least 5.22 population doublings (37-fold) under optimal large scale conditions.
Figure 6:
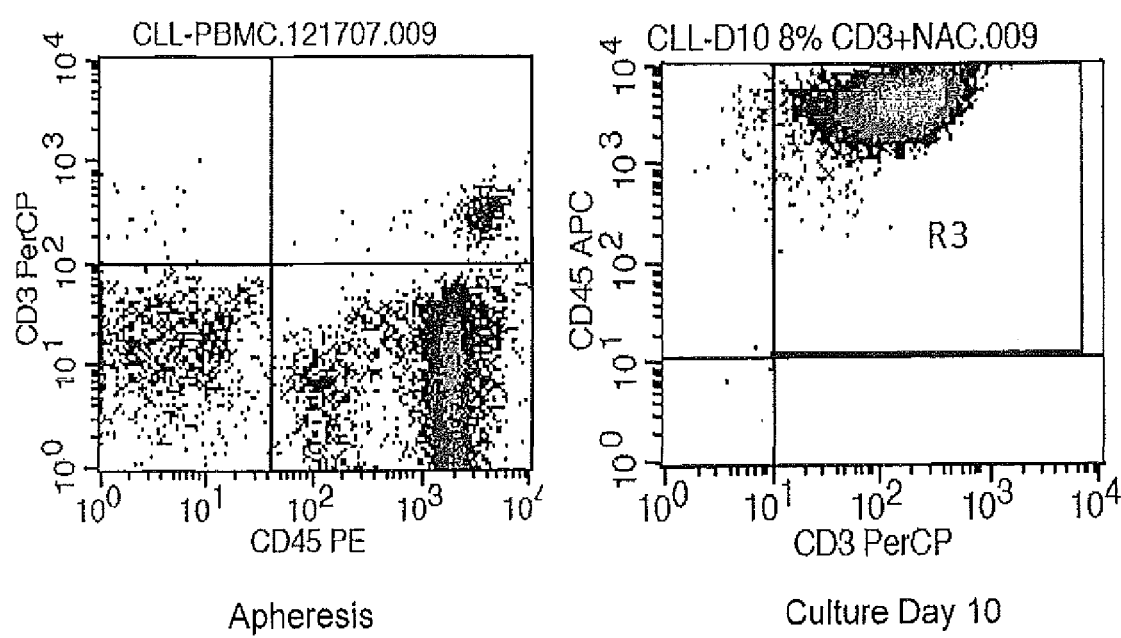
FIG. 6 is an image demonstrating the percentage of CD3+ T cells of the CD45+ cells increased from 4.3% in the apheresis product to >99% in the expanded T cell product after 10 days of culture.

The next set of experiments was designed to use a single dose of 5×10$^9$ to 2.0×10$^{10}$ expanded T-cells, as this dose has been shown to be safe and well-tolerated in several trials to patients with hematologic malignancies and HIV. FIG. 4 shows that T cells selected and expanded with anti-CD3/CD28 beads were able to be expanded at least 4.3 population doublings (20-fold) under optimal conditions in small scale. FIG. 5 is a chart demonstrating that T cells selected and expanded with anti-CD3/CD28 beads using the optimal small scale conditions in a clinical scale bioreactor can expand at least 5.22 population doublings (37-fold) under optimal large scale conditions. Furthermore, the percentage of CD3+ T cells of the CD45+ cells increased from 4.3% in the apheresis product to >99% in the expanded T cell product after 10 days of culture (FIG. 6). Importantly, the CD19+ cells declined to less than 0.5% at Day 10 of culture.

The next set of experiments was designed to determine the safety and feasibility of an infusion of 5×10$^9$ to 2.0×10$^{10}$ activated T cells administered to the study subject following therapy with fludarabine/cyclophosphamide (fly/cy). The experiments were also designed to determine if administration of expanded T cells following flu/cy-induced lymphodepletion can improve T lymphocyte numbers. Effect of T cell infusion on immune function, and disease progression and survival can be evaluated. Briefly, the methods of the study are as follows.

The materials and methods employed in these experiments are now described.

Apheresis Collection

Study subjects undergo steady-state apheresis procedure of 10-12 liters, an amount that is processed on a routine basis, prior to starting a single course of chemotherapy with fludarabine/cyclophosphamide. The goal for collection is at least 1×10$^9$ CD3+ T-cells. Assuming an expected CD3% of 3-10% of mononuclear cells, at least 15×10$^9$ mononuclear cells should be collected. Peripheral samples are taken for baseline immunoassays.

PBMC Enrichment

The apheresis product is first ficoll separated before further processing to obtain the PBMCs as well as to remove plasma, platelets and red blood cell contamination.

Positive Selection of CD3+ T-Cells

Following the PBMC enrichment, and real time flow cytometry analysis, approximately 4-8% of CD3+T-cells, based on a pre-clinical study, are targeted for positive selection according to an established SOP by using Dynal M450 osylactivated magnetic beads conjugated with anti-human CD3 and CD28 antibodies at a cell to beads ratio of 1:3 to substantially reduce B leukemic cell content from the positively selected CD3+ T-cell population prior to the initiation of ex-vivo culture expansion.

Ex-vivo Expansion of CD3+ T Cells

After the CD3/28 positive selection, positively selected CD3+ T-cells are seeded into gas permeable flasks such as the Baxter Lifecell Flask or a suitable replcement. Cells are grown in X-VIVO™ media supplemented with 5% commercial pooled human AB serum. The cells are counted and fresh media added throughout the expansion to maintain cells at an appropriate density.

Final Product Preparation and Release Testing

Cells are expanded ex vivo for up to 11 days and then harvested on the designated infusion date. There may be certain circumstances that require that the final product be cryopreserved for thawing and infusion on a later date. Culture samples are taken for flow cytometry, endotoxin, bacterial and fungal testing to determine whether final product release criteria are met. On the harvest day, the microbeads are removed with a Baxter Fenwal Maxsep® magnetic cell separator. The cells are then be washed and concentrated with the Baxter Fenwal Harvester System, and resuspended in 100-500 mL 1:1 Plasmalyte A/Dextrose 5%, 0.45% NaCl containing 0.5-1% human serum albumin. Cells for later additional infusions may be cryopreserved in an infusible media 1:1 Plasmalyte A/Dextrose 5%, 0.45% NaCl containing 0.5-1% human serum albumin, dextran, and 7.5% DMSO. Final products are not released until all records are reviewed and signed off by the CVPF Quality Manager, CVPF Director, and external Quality Assurance consultant. The expanded T cells are transported to the subject's bedside, either in the subject's hospital room or at the GCRC.

The criteria for release of the expanded T-cells for reinfusion include all of the following:

Minimum cell viability of ≥80% on Final Product (fresh), ≥70% for cryopreserved product CD3%>80% by FACS on day 7 or later Less than 100 residual microbeads/3×10$^6$ cells The number of CLL cells as defined by CD19 expression in the final infused product will be less than the number of CD19+ cells in the apheresis product No growth of bacterial and fungal cultures sent 96-48 hours preharvest The gram stain of a sample of the pre-harvest cells must be negative The endotoxin assay from day −1 or −2 to harvest must be <1 EU/ml or the endotoxin of the final product must be less than 5 EU/kg In addition, there are a number of post-release follow-up tests on the pre-harvest or final product that are not be available until after subject infusion.

These include:

| Samples | Criteria |
|---|---|
| CD3% | >80% by FACS |
| Mycoplasma | Negative (sample from pre-harvest) |
| Bacterial Culture | Negative for growth (sample from final product)) |
| Fungal Culture | Negative for growth (sample from final product) |
| Endotoxin | <1 EU/ml (sample from final product) |

Packaging and Administration

The T cells are administered via intravenous infusion over 20-30 minutes without a leukocyte filter. Each infusion bag are affixed to it a label containing the following: "FOR AUTOLOGOUS USE ONLY." In addition, the label have at least two unique identifiers such as the subject's initials, birth date, and study number. Prior to infusion, two individuals are independently verified for this information.

Screening

The following are performed during the screening visit(s):

Obtain informed consent prior to proceeding with screening for eligibility (performed before any other study procedures occur)

Confirm a diagnosis of Chronic Lymphocytic Leukemia and Progressive Multifocal Leukoencephalopahty (PML)

Perform a full medical history and physical exam, including careful review of current medications.

Check adequacy of veins for leukapheresis or schedule temporary pheresis catheter placement Confirm an ECOG performance status <2.

Confirm that study subject meets all other inclusion/exclusion criteria

Complete a comprehensive laboratory evaluation, including complete blood count, blood chemistries, liver function tests, and PT/PTT DTH intradermal skin test to test for immune response evaluation. Readout 48 hours later.

Imaging studies to determine current disease status (e.g. CT/MRI/BM Bx as medically indicated).

Chemotherapy

Subjects receive a single course of outpatient conditioning lymphodepletion chemotherapy with intravenous cyclophosphamide (250 mg/m$^2$/d for 3 days) and intravenous fludarabine (25 mg/m$^2$/d for 3 days), both administered on days −4 to −2.

Activated T cell Infusion

Activated T cells are infused ~2 days after the last dose of fludarabine/cyclophosphamide. Prior to the activated T cell infusion subjects are premedicated with acetaminophen 650 mg PO and diphenhydramine 25-50 mg PO/IV. Activated T cells are administered via intravenous infusion over 20-30 minutes without a leukocyte filter. Subjects are observed for 30 minutes after completion of the infusion. Corticosteroids is available at the bedside in the event of an allergic-type reaction but should not be administered on a routine basis.

Follow Up Day +60

A full medical history and physical exam is performed, including careful review of current medications. A comprehensive laboratory evaluation is performed, including complete blood count, blood chemistries, liver function tests. DTH intradermal skin test is conducted to test for immune recovery. Read-out are taken 48 hours after.

Follow Up Day +180

A full medical history and physical exam is performed, including careful review of current medications. A comprehensive laboratory evaluation is performed, including complete blood count, blood chemistries, liver function tests. Imaging studies are conducted to determine disease status (e.g. CT/MRI/BM Bx as medically indicated). Neurologic evaluation (MRI) and viral studies are performed to determine status of PML.

Immunological and PML Assessments

Samples from the apheresis collection at Day −10, and blood draws from time of screening (both pre-chemotherapy and used as baseline), Day +60 and Day +180 are used for immunological assessments to determine whether the administration of expanded T cells improves T lymphocyte numbers and immune function of the study subject. Samples from standard of care blood draws at Day +7, +14, +21 and Day +30 may also be cryopreserved and used for additional interim assessments if needed. Samples from the bone marrow biopsy at Day +180 are cryopreserved for future immunoassessments.

DTH-response to *Candida albicans* or to another suitable recall antigen is measured at baseline and on day 60+/−5days after T-cell infusion.

Subjects are evaluated by neurology pre and post therapy for determination of PML. An MRI can be used for assessment of lesions. JCV p36 and p100 tetramer staining can be used to assess immune response to JC virus.

Lymphocyte Studies

Lymphocyte subsets (CD3/CD4/CD8) are monitored and compared to baseline, using absolute lymphocyte count and flow cytometry. Lymphocyte cytokine studies are measured pre chemotherapy and 60+/−5 days and 180+/− days post T-cell infusion using an automated ELISPOT method to determine the frequency of T-cells that secrete cytokines (such as IFNγ) after in vitro polyclonal stimulation. CD4 T-cell receptor (TCR) repertoire analysis are done at baseline and then on day 60+/−5 days and 180+/− days after T-cell infusion.

Expanded T Cells Following flu/cy—Induced Lymphodepletion Can Improve T Lymphocyte Numbers Subjects undergo steady-state mononuclear cell apheresis of approximately 10-12 liters on the Baxter Amicus or Cobe Spectra. It is desirable to collect approximately $1 \times 10^9$ T cells or more. Depending on the study subject's CD3 percent and absolute number, this may correspond to approximately $15\text{-}20 \times 10^9$ mononuclear cells or more. Following apheresis, the subjects undergo a single course of combination chemotherapy with fludarabine/cyclophosphamide (intravenous cyclophosphamide (250 mg/m$^2$/d for 3 days) and intravenous fludarabine (25 mg/m$^2$/d for 3 days). The apheresis product is ficoll separated and an initial CD3+ T cell population of approximately 4-8% is targeted for expansion, depending on the current CD3 percent as measured by flow cytometry. Cells are positively selected and expanded using anti-CD3 and anti-CD28 antibody-coated magnetic beads according to a previously published and validated process (Laport et al., 2003, Blood 102:2004-13; Kalamasz et al., 2004, J. Immunother. 27:405-18) in order to substantially reduce leukemic B cell content from the expanded T cell culture and therefore from the final infused product. Approximately two days after ending flu/cy therapy, the subjects receive one infusion of $5 \times 10^9$ to $2.0 \times 10^{10}$ activated T cells. Additional cells may be cryopreserved for additional doses if needed. Cell phenotyping is conducted on the pre- and post- expanded T cells, and throughout the 10-14 day culture (JCV p36 and p100 tetramer staining, CD3, CD4, CD8, CD28. CD62L, CD4OL, CD19).

Figure 7:
FIG. 7 is a schematic of the general study of using Fludarabine-Cyclophosphamide followed by adoptive transfer of CD3/CD28 ex vivo costimulated autologous T cells for Chronic Lymphocytic Leukemia (CLL) and Progressive Multifocal Leukoencephalopathy (PML).

At 60 days after T cell infusion (approximately Day +60), immune recovery is monitored by testing delayed-type hypersensitivity (DTH) to recall antigen and JCV tetramer staining and ELISPOT as compared to baseline. Clinical staging by MRI and immune system safety assessments (for autoimmune events) takes place 6 months after T cell infusion (approximately Day +180). The general study scheme is depicted in FIG. 7.

Feasibility of the study is partly based on the production of cells that meet the minimum release criteria for reinfusion. Besides the standard T cell product release criteria, an additional CLL minimal residual disease (MRD) criteria is that that total CLL cells in the expanded product as defined by CD 19+ be less than the number of CLL cells removed by apheresis. Safety is defined as the incidence of ≥Grade 3 treatment-related serious adverse events. Immune recovery is monitored by comparing to baseline the quantity of lymphocyte subsets, using absolute lymphocyte count and flow cytometry. Primary endpoint evaluation is based on Day+60 values.

Immune function is assessed by a variety of research based lab assays, including TCR repertoire, T cell mitogen responses, DTH response, and JCV tetramer staining and ELISPOT for cytokine secretion.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method for treating Chronic Lymphocytic Leukemia (CLL) comprising administering to a patient with CLL a single dose comprising a population of about $5 \times 10^9$ to about $2 \times 10^{10}$ autologous T cells activated and expanded according to a method comprising,
    (a) activating a population of T cells in vitro with an agent which stimulates a TCR/CD3 complex-associated signal in the T cells, wherein the agent is attached on a surface; and
    (b) stimulating a CD28 accessory molecule on the surface of the T cells in vitro with a ligand that binds the CD28 accessory molecule on the surface of the T cells, wherein the ligand is attached on the same surface as the agent; and
wherein the activating and stimulating steps thereby induce proliferation of the T cells such that T cell counts are increased in the CLL patient at least one month after administration.

2. The method of claim 1 wherein the agent is selected from the group consisting of an anti-CD3 antibody or antigen-binding fragment thereof, an anti-TCR antibody or antigen-binding fragment thereof, a superantigen, an MHC-peptide tetramer, and an antigen in a form suitable to trigger a primary activation signal in the T cell when complexed with the TCR/CD3 complex.

3. The method of claim 1 wherein the ligand is selected from the group consisting of an anti-CD28 antibody or antigen-binding fragment thereof, CD80 or a CD28-binding fragment thereof, and CD86 or a CD28-binding fragment thereof.

4. The method of claim 1 wherein the surface is selected from the group consisting of a bead, a lipid bilayer, a cell surface, and a tissue-culture dish.

5. The method of claim 1 wherein the activated and expanded T cells are administered intravenously.

6. The method of claim 4 wherein said cell surface is of a human cell line.

7. The method of claim 6 wherein said human cell line is K562.

8. The method of claim 6 wherein said cell is genetically modified to express a human Fcγ receptor.

9. The method of claim 8 wherein said human Fcγ receptor comprises CD32 or CD64.

10. The method of claim 6 wherein said cell is further genetically modified to express a co-stimulatory molecule selected from the group consisting of CD80, CD86, 4-1BBL, OX40L, ICOS-L, ICAM, PD-L1 and PD-L2.

11. The method of claim 6 wherein said cell has been genetically modified to express a cytokine.

12. The method of claim 11 wherein said cytokine is selected from the group consisting of IL-2, GM-CSF, IL-4, TNF-α, and IFN-γ.

* * * * *